United States Patent
Li et al.

(10) Patent No.: US 11,471,513 B2
(45) Date of Patent: Oct. 18, 2022

(54) HIGHLY GLYCOSYLATED HUMAN BLOOD-CLOTTING FACTOR VIII FUSION PROTEIN, AND MANUFACTURING METHOD AND APPLICATION OF SAME

(71) Applicants: AMPSOURCE BIOPHARMA SHANGHAI INC., Shanghai (CN); FUREN PHARMACEUTICAL GROUP CO., LTD, Luyi Zhoukou (CN); PHARMAB, INC., Shanghai (CN); KAIFENG PHARMACEUTICAL (GROUP) CO., LTD., Kaifeng (CN)

(72) Inventors: Qiang Li, Shanghai (CN); Wenchen Zhu, Luyi Zhoukou (CN); Yuanli Li, Shanghai (CN); Chenggong Zhu, Luyi Zhoukou (CN); Yongjuan Gao, Shanghai (CN); Zijia Ren, Kaifeng (CN); Luyan Zhu, Kaifeng (CN); Naichao Sun, Shanghai (CN); Xiaoshan Wang, Kaifeng (CN); Bin Liu, Kaifeng (CN); Zhi Li, Kaifeng (CN); Wenwen Wang, Kaifeng (CN); Ming Jiang, Kaifeng (CN); Qilei Wang, Kaifeng (CN); Lirui Wang, Kaifeng (CN); Shuya Wang, Kaifeng (CN); Songlin Zhu, Kaifeng (CN); Jie Gao, Kaifeng (CN); Hongsheng Su, Kaifeng (CN)

(73) Assignees: Ampsource Biopharma Shanghai Inc., Shanghai (CN); Furen Pharmaceutical Group Co., Ltd, Luyi Zhoukou (CN); Pharmab, Inc., Shanghai (CN); Kaifeng Pharmaceutical (Group) Co., Ltd., Kaifeng (CN)

( * ) Notice: Subject to any disclaimer, the term of this patent is extended or adjusted under 35 U.S.C. 154(b) by 662 days.

(21) Appl. No.: 16/479,494

(22) PCT Filed: Nov. 16, 2016

(86) PCT No.: PCT/CN2016/106010
§ 371 (c)(1),
(2) Date: Jul. 19, 2019

(87) PCT Pub. No.: WO2018/032637
PCT Pub. Date: Feb. 22, 2018

(65) Prior Publication Data
US 2019/0365867 A1 Dec. 5, 2019

(30) Foreign Application Priority Data
Aug. 19, 2016 (CN) .......................... 201610692838.0

(51) Int. Cl.
*A61K 38/37* (2006.01)
*A61K 47/68* (2017.01)
(Continued)

(52) U.S. Cl.
CPC .............. *A61K 38/37* (2013.01); *A61K 47/65* (2017.08); *A61K 47/6811* (2017.08); *A61P 7/04* (2018.01);
(Continued)

(58) Field of Classification Search
CPC ........ A61K 38/37; A61K 38/00; A61K 47/65; A61K 47/6811; A61P 7/04; C07K 14/755;
(Continued)

(56) References Cited

U.S. PATENT DOCUMENTS

| 4,399,216 A | 8/1983 | Axel et al. |
| 4,818,679 A | 4/1989 | Chasin et al. |

(Continued)

FOREIGN PATENT DOCUMENTS

| CN | 1290301 A | 4/2001 |
| CN | 1889937 A | 1/2007 |

(Continued)

OTHER PUBLICATIONS

Machine Translation of CN104292341A, translation by EPO on Jun. 8, 2021, attached as pdf, 11 pages including Specification and Claims (Year: 2021).*

(Continued)

*Primary Examiner* — Randall L Beane
(74) *Attorney, Agent, or Firm* — Jenkins, Wilson, Taylor & Hunt, PA

(57) ABSTRACT

A highly glycosylated human blood-clotting factor VIII (FVIII) fusion protein, and a manufacturing method and
(Continued)

application of same. The fusion protein comprises, from the N-terminus to the C-terminus, a human (FVIII), a flexible peptide connector, at least one rigid unit of a human chorionic gonadotropin β-subunit carboxyl terminal peptide, and a half-life extending portion (preferentially selected from a human IgG Fc variant). The fusion protein has a similar level of biological activity as a recombinant (FVIII) and an extended in vivo half-life, thereby improving pharmacokinetics and drug efficacy.

4 Claims, 7 Drawing Sheets

Specification includes a Sequence Listing.

(51) Int. Cl.
| | | |
|---|---|---|
| *A61K 47/65* | (2017.01) | |
| *A61P 7/04* | (2006.01) | |
| *C07K 14/59* | (2006.01) | |
| *C07K 14/755* | (2006.01) | |
| *C07K 19/00* | (2006.01) | |
| *C12N 15/62* | (2006.01) | |
| *C12N 15/85* | (2006.01) | |

(52) U.S. Cl.
CPC ............ *C07K 14/59* (2013.01); *C07K 14/755* (2013.01); *C07K 19/00* (2013.01); *C12N 15/62* (2013.01); *C12N 15/85* (2013.01)

(58) Field of Classification Search
CPC ...... C07K 19/00; C07K 14/59; C07K 14/745; C07K 2319/00; C07K 2317/52; C07K 2319/30; C07K 2319/31; C07K 7/06; C07K 7/08; A01K 2217/075; A01K 2227/105; A01K 2267/0381; C12N 15/62; C12N 15/85
See application file for complete search history.

(56) References Cited

U.S. PATENT DOCUMENTS

| | | | |
|---|---|---|---|
| 6,103,501 A | 8/2000 | Boime et al. | |
| 6,225,449 B1 | 5/2001 | Boime | |
| 7,189,827 B2 | 3/2007 | Feige | |
| 7,582,607 B2 | 9/2009 | Frye et al. | |
| 8,163,889 B2 | 4/2012 | Kim et al. | |
| 8,273,854 B2 | 9/2012 | Glaesner et al. | |
| 8,304,224 B2 | 11/2012 | Lovgren | |
| 8,476,234 B2 | 7/2013 | Fima et al. | |
| 9,023,791 B2 | 5/2015 | Boettcher et al. | |
| 9,266,935 B2 | 2/2016 | Boettcher et al. | |
| 9,279,013 B2 | 3/2016 | Walker et al. | |
| 9,493,543 B2 | 11/2016 | Bolt et al. | |
| 9,573,987 B2 | 2/2017 | Dimarchi et al. | |
| 9,580,483 B2 | 2/2017 | Ling et al. | |
| 9,675,676 B2 | 6/2017 | Pierce et al. | |
| 9,803,023 B2 | 10/2017 | Chamberlain et al. | |
| 9,867,873 B2 | 1/2018 | Pierce et al. | |
| 9,915,665 B2 | 3/2018 | Benatuil et al. | |
| 10,010,622 B2 | 7/2018 | Dumont et al. | |
| 10,023,624 B2 | 7/2018 | Hou et al. | |
| 10,287,564 B2 | 5/2019 | Hong et al. | |
| 11,123,438 B2 * | 9/2021 | Li ........................... A61P 3/04 | |
| 2001/0012628 A1 | 8/2001 | Agarwal et al. | |
| 2003/0211580 A1 | 11/2003 | Lustbader | |
| 2005/0250185 A1 | 11/2005 | Murphy et al. | |
| 2007/0129298 A1 | 6/2007 | Krebber et al. | |
| 2009/0042784 A1 | 2/2009 | Krarup | |
| 2010/0081614 A1 | 4/2010 | Fares et al. | |
| 2010/0317585 A1 * | 12/2010 | Fima ........................ A61P 7/02 |
| | | | 435/320.1 |
| 2013/0108629 A1 * | 5/2013 | Dumont ..................... A61P 7/00 |
| | | | 424/134.1 |
| 2013/0202596 A1 * | 8/2013 | Salas ........................ C07K 16/18 |
| | | | 424/134.1 |
| 2013/0252884 A1 | 9/2013 | Garibay et al. | |
| 2013/0274194 A1 | 10/2013 | Dumont et al. | |
| 2013/0281671 A1 * | 10/2013 | Peters ....................... C12N 9/60 |
| | | | 530/383 |
| 2014/0294821 A1 * | 10/2014 | Dumont ................. A61K 47/6803 |
| | | | 514/14.1 |
| 2014/0303084 A1 * | 10/2014 | Thorn ................... C07K 14/745 |
| | | | 435/352 |
| 2014/0308280 A1 * | 10/2014 | Maloney ................. A61K 38/37 |
| | | | 424/134.1 |
| 2014/0357843 A1 | 12/2014 | Oh et al. | |
| 2014/0370035 A1 * | 12/2014 | Jiang ........................ A61P 37/06 |
| | | | 424/178.1 |
| 2014/0378663 A1 | 12/2014 | Fontayne et al. | |
| 2015/0079072 A1 * | 3/2015 | Sommer ................. G01N 33/86 |
| | | | 424/133.1 |
| 2015/0185235 A1 * | 7/2015 | Sommer ................. G01N 33/86 |
| | | | 424/145.1 |
| 2015/0191526 A1 * | 7/2015 | Low ...................... C07K 14/755 |
| | | | 514/14.1 |
| 2015/0203558 A1 | 7/2015 | Fares et al. | |
| 2015/0266943 A1 * | 9/2015 | Chhabra .................. A61K 38/36 |
| | | | 514/14.1 |
| 2015/0353911 A1 * | 12/2015 | Salas ........................ A61K 47/62 |
| | | | 435/367 |
| 2016/0000884 A1 | 1/2016 | Rischel et al. | |
| 2016/0115467 A1 | 4/2016 | Salas | |
| 2016/0296607 A1 * | 10/2016 | Jiang ............... C12Y 304/21022 |
| 2019/0184026 A1 | 6/2019 | Li et al. | |
| 2020/0157185 A1 | 5/2020 | Gao et al. | |

FOREIGN PATENT DOCUMENTS

| | | |
|---|---|---|
| CN | 101010338 A | 8/2007 |
| CN | 1802386 B | 12/2010 |
| CN | 102625811 A | 8/2012 |
| CN | 102639144 A | 8/2012 |
| CN | 102802657 A | 11/2012 |
| CN | 103140237 A | 6/2013 |
| CN | 103328502 A | 9/2013 |
| CN | 103539860 A | 1/2014 |
| CN | 103539861 A | 1/2014 |
| CN | 103539868 A | 1/2014 |
| CN | 103539869 A | 1/2014 |
| CN | 103649127 A | 3/2014 |
| CN | 103827142 A | 5/2014 |
| CN | 103897064 A | 7/2014 |
| CN | 103945871 A | 7/2014 |
| CN | 104039831 A | 9/2014 |
| CN | 104114183 A | 10/2014 |
| CN | 104292341 A * | 1/2015 |
| CN | 104427994 A | 3/2015 |
| CN | 104519897 A | 4/2015 |
| CN | 104519912 A | 4/2015 |
| CN | 104693270 A | 6/2015 |
| CN | 104774269 A | 7/2015 |
| CN | 104903352 A | 9/2015 |
| CN | 105153313 A | 12/2015 |
| CN | 103897064 B | 5/2016 |
| CN | 105753945 A | 7/2016 |
| CN | 104024273 B | 10/2016 |
| CN | 106117370 A | 11/2016 |
| CN | 106256835 A | 12/2016 |
| CN | 106279436 A | 1/2017 |
| CN | 106317226 A | 1/2017 |
| CN | 106117370 B | 5/2017 |
| CN | 106317226 B | 9/2017 |
| CN | 107474138 A | 12/2017 |
| CN | 105753945 B | 4/2019 |
| CN | 110028587 A | 7/2019 |
| CN | 108137708 B | 10/2019 |
| CN | 110229238 B | 10/2020 |
| EA | 005404 B1 | 2/2005 |
| EA | 201291480 A1 | 9/2013 |

(56) References Cited

FOREIGN PATENT DOCUMENTS

| | | | |
|---|---|---|---|
| EP | 1 624 891 B1 | 8/2009 | |
| EP | 2822576 B1 | 1/2018 | |
| EP | 2808343 B1 | 5/2019 | |
| EP | 3 502 143 A1 | 6/2019 | |
| EP | 3 620 474 A1 | 3/2020 | |
| JP | 2014-522838 A | 9/2014 | |
| JP | 2019-531087 A | 10/2019 | |
| KR | 2010-0099179 A | 9/2010 | |
| KR | 10-1027427 B1 | 4/2011 | |
| KR | 20190042629 A | 4/2019 | |
| RU | 2312868 C2 | 12/2007 | |
| WO | WO 03/011213 A2 | 2/2003 | |
| WO | WO 03/061712 A1 | 7/2003 | |
| WO | WO 2004/110472 A2 | 12/2004 | |
| WO | WO 2005/000892 A2 | 1/2005 | |
| WO | WO 2005/058953 A2 | 6/2005 | |
| WO | WO 2005/091944 A2 | 10/2005 | |
| WO | WO 2005/113606 A2 | 12/2005 | |
| WO | WO 2006/028595 A2 | 3/2006 | |
| WO | WO 2006/028714 A1 | 3/2006 | |
| WO | WO 2006/050247 A2 | 5/2006 | |
| WO | WO 2006/053391 A2 | 5/2006 | |
| WO | WO 2006/065582 A2 | 6/2006 | |
| WO | WO 2007/090584 A1 | 8/2007 | |
| WO | WO 2008/121563 A2 | 10/2008 | |
| WO | WO 2009/149171 A2 | 12/2009 | |
| WO | WO 2010/042747 A2 | 4/2010 | |
| WO | WO 2010/084169 A2 | 7/2010 | |
| WO | WO 2010/129503 A1 | 11/2010 | |
| WO | WO 2010/129600 A2 | 11/2010 | |
| WO | WO 2010/142665 A1 | 12/2010 | |
| WO | WO 2011/071783 A1 | 6/2011 | |
| WO | WO 2011/092234 A1 | 8/2011 | |
| WO | WO 2011/130417 A2 | 10/2011 | |
| WO | WO 2012/010553 A1 | 1/2012 | |
| WO | WO 2012/066075 A1 | 5/2012 | |
| WO | WO 2012/158704 A1 | 11/2012 | |
| WO | WO 2012/170438 A2 | 12/2012 | |
| WO | WO 2012/175751 A2 | 12/2012 | |
| WO | WO 2013/049234 A2 | 4/2013 | |
| WO | WO 2013/049247 A1 | 4/2013 | |
| WO | WO 2013/096386 A1 | 6/2013 | |
| WO | WO 2013/100702 A1 | 7/2013 | |
| WO | WO 2013/121416 | 8/2013 | |
| WO | WO-2013123457 A1 * | 8/2013 | ............. A61K 35/14 |
| WO | WO 2013/152351 A2 | 10/2013 | |
| WO | WO 2013/185114 A2 | 12/2013 | |
| WO | WO 2013/188181 A1 | 12/2013 | |
| WO | WO 2014/026954 A1 | 2/2014 | |
| WO | WO 2014/037373 A1 | 3/2014 | |
| WO | WO 2014/052490 A1 | 4/2014 | |
| WO | WO 2014/106015 A2 | 7/2014 | |
| WO | WO-2015023894 A1 * | 2/2015 | ............. A61K 38/36 |
| WO | WO 2015/062350 A1 | 5/2015 | |
| WO | WO-2016020210 A1 * | 2/2016 | ............. A61K 38/37 |
| WO | WO 2016/114633 A1 | 7/2016 | |
| WO | WO 2017/074123 A1 | 5/2017 | |
| WO | WO 2018/032637 A1 | 2/2018 | |
| WO | WO 2018/032638 A1 | 2/2018 | |
| WO | WO 2018/032785 A1 | 2/2018 | |
| WO | WO 2018/032786 A1 | 2/2018 | |

OTHER PUBLICATIONS

Coyle et al., "An open-label phase I study to evaluate the pharmacokinetics and safety profile of Bay 94-9027, a PEGylated B-domain-deleted recombinant factor VIII, in previously treated patients with severe hemophilia A," Haemophilia, vol. 18 (Suppl. 3), FP-MO-03.2-3, p. 22 (2012).

Coyle et al., "Phase I study of BAY 94-9027, a PEGylated B-domain-deleted recombinant factor VIII with an extended half-life, in subjects with hemophilia A," Journal of Thrombosis and Haemostasis, vol. 12, pp. 488-496 (2014).

Datta-Mannan et al., "Influence of improved FcRn binding on the subcutaneous bioavailability of monoclonal antibodies in cynomolgus monkeys," mAbs, vol. 4, No. 2, pp. 267-273 (2012).

Dumont et al., "Prolonged activity of a recombinant factor VIII-Fc fusion protein in hemophilia A mice and dogs," Blood, vol. 119, No. 13, pp. 3024-3030 (2012).

Fares et al., "Design of a long-acting follitropin agonist by fusing the C-terminal sequence of the chorionic gonadotropin β subunit to the follitropin β subunit," Proc. Natl. Acad. Sci. USA, vol. 89, pp. 4304-4308 (1992).

Gilbert et al., "Specific Membrane Binding of Factor VIII Is Mediated by 0-Phospho-$_L$-serine, a Moiety of Phosphatidylserine," Biochemistry, vol. 32, pp. 9577-9585 (1993).

Hinton et al., "Engineered Human IgG Antibodies with Longer Serum Half-lives in Primates," The Journal of Biological Chemistry, vol. 279, No. 8, pp. 6212-6216 (2004).

Hinton et al., "An Engineered Human IgG1 Antibody with Longer Serum Half-Life," The Journal of Immunology, vol. 176, pp. 346-356 (2006).

Jefferis et al., "IgG-Fc-mediated effector functions: molecular definition of interaction sites for effector ligands and the role of glycosylation," Immunol. Rev., vol. 163, pp. 59-76 (1998).

Peters et al., "Biochemical and functional characterization of a recombinant monomeric factor VIII-Fc fusion protein," Jounral of Thrombosis and Haemostasis, vol. 11, pp. 132-141 (2012).

Powell et al., "Safety and prolonged activity of recombinant factor VIII Fc fusion protein in hemophilia A patients," Blood, vol. 119, No. 13, pp. 3031-3037 (2012).

Roopenian et al., "FcRn: the neonatal Fc receptor comes of age," Nat. Rev. Immunol., vol. 7, No. 9, pp. 715-725 (2007).

Sambrook et al., Molecular Cloning: A Laboratory Manual, Second Edition, vol. 1, Cold Spring Harbor Laboratory Press (1989).

Shields et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 276, No. 9, pp. 6591-6604 (2001).

Tiede et al., "Enhancing the pharmacokinetic properties of recombinant factor VIII: first-in-human trial of glycoPEGylated recombinant factor VIII in patients with hemophilia A," Journal of Thrombosis and Haemostasis, vol. 11, pp. 670-678 (2013).

Turecek et al., "BAX 855, a PEGylated rFVIII product with prolonged half-life," Hämostaseologie, Vo. 32 (Suppl. 1), pp. S29-S38 (2012).

Chinese Office Action for Application No. 201610692838.0 dated May 31, 2017.

International Preliminary Report on Patentability, Written Opinion, and International Search Report for Application No. PCT/CN2016/106010 dated Feb. 19, 2019.

Collins et al., "Recombinant long-acting glycoPEGylated factor IX in hemophilia B: a multinational randomized phase 3 trial," Blood, vol. 124, No. 26, pp. 3880-3886 (2014).

Peters et al., "Prolonged activity of factor IX as a monomeric Fc fusion protein," Blood, vol. 115, No. 10, pp. 2057-2064 (2010).

Written Opinion and International Search Report for Application No. PCT/CN2017/079872 dated Jul. 5, 2017.

Calo et al., "Enhancing the longevity and in vivo potency of therapeutic proteins: The power of CTP," Precision Medicine, vol. 2, Edition 989, (Sep. 30, 2015).

Korean Office Action for Application No. 20197007918 dated Jul. 17, 2020.

Non-Final Office Action for U.S. Appl. No. 16/604,081 dated Aug. 13, 2020.

Skosyrev et al., "The Dependence of Stability of the Green Fluorescent Protein-Obelin Hybrids on the Nature of Their Constituent Modules and the Structure of the Amino Acid Linker", Russian Journal of Bioorganic Chemistry, vol. 27, No. 5, pp. 323-329, (2001).

Treetharnmathurot et al., "Effect of PEG molecular weight and linking chemistry on the biological activity and thermal stability of PEGylated trypsin", International Journal of Pharmaceutics, vol. 357, pp. 252-259 (2008).

(56) References Cited

OTHER PUBLICATIONS

Wen et al., "Discovery and Investigation of O-Xylosylation in Engineered Proteins Containing a (GGGGS) Linker", Analytical Chemistry, vol. 85, pp. 4805-4812, (2013).
Chinese Office Action for Application No. 201610692679.4 dated Dec. 27, 2016.
International Search Report for Application No. PCT/CN2016/106011 dated Feb. 17, 2017.
International Search Report for Application No. PCT/CN2017/079871 dated Jun. 2, 2017.
Chinese Office Action for Application No. 201780000362.2 dated Jul. 11, 2019.
Russian Office Action for Application No. 2019106765/10(013011) dated Dec. 25, 2019.
Japanese Office Action for Application No. 2019-530527 dated Mar. 23, 2020.
Restriction Requirement for U.S. Appl. No. 16/604,081 dated May 12, 2020.
Arai et al., "Design of the linkers which effectively separate domains of a bifunctional fusion protein", Protein Engineering, vol. 14, No. 8, pp. 529-532 (2001).
Beenken et al., "The FGF family: biology, pathophysiology and therapy", Nature Reviews Drug Discover, vol. 8, pp. 235 (2009).
Berglund et al., "Fibroblast Growth Factor 21 Controls Glycemia via Regulator of Hepatic Glucose Flux and insulin Sensitivity", Endocrinology, vol. 150, pp. 4084-4093 (2009).
Broze et al., "Purification and Properties of Human Coagulation Factor VII", The Journal of Biological Chemistry, vol. 255, No. 4, pp. 1242-1247 (1980).
Chen et al., Fusion protein linkers: property, design and functionality, Advanced drug delivery reviews, vol. 65, No. 10, pp. 1357-1369 (2013).
Coskun et al., "Fibroblast Growth Factor 21 Corrects Obesity in Mice" Endocrinology, vol. 149, pp. 6018-6027 (2008).
Dickneite et al., "Prothrombin complex concentrate versus recombinant factor VIIa for reversal of coumarin anticoagulation", Thrombosis Research, vol. 119, pp. 643-651 (2007).
Dutchak et al., "Fibroblast Growth Factor-21 Regulates PPAR Activity and the Antidiabetic Actions of Thiazolidinediones", Cell, vol. 148, pp. 556-567 (2012).
Gaich et al., "The Effects of LY2405319, an FGF21 Analog, in Obese Human Subjects with Type 2 Diabetes", Cell Metabolism, vol. 18, pp. 333-340 (2013).
Golor et al., "Safety and pharmacokinetics of a recombinant fusion protein linking coagulation factor VIIa with albumin in healthy volunteers", Journal of Thrombosis and Haemostasis, vol. 11, pp. 1977-1985 (2013).
Hagen et al., "Characterization of a cDNA coding for human factor VII", Proc. Natl. Acad. Sci. vol. 83, pp. 2412-2416 (1986).
Hart et al., "Acquired Hemophilia", Haemophilia, vol. 18. Suppl. 3, pp. 1-208 (2012).
Hecht et al., "Rationale-Based Engineering of a Potent Long-Acting FGF21 Analog for the Treatment of Type 2 Diabetes", PLOS One, vol. 7, Issue 11, pp. e49345 (2012).
Hedner et al., "Use of human factor VIIa in the treatment of two hemophilia A patients with high-titer inhibitors", The Jornal of Clinical Investigstion, vol. 71, pp. 1836-1841 (1983).
Kharitonenkov et al., "FGF-21 as a novel metabolic regulator", The Journal of Clinical Investigation, vol. 115, No. 6, pp. 1627-1635 (2005).
Kharitonenkov et al., "The Metabolic State of Diabetic Monkeys Is Regulated by Fibroblast Growth Factor-21", Endocrinology, vol. 148, pp. 774-781 (2007).
Kisiel et al., "Enzymological aspects of blood coagulation", Behring Institute Mitteilungen, vol. 73, pp. 29-42 (1983).
Klein et al., "Design and characterization of structured protein linkers with different flexibilities", Protein Engineering, Design and Selection, vol. 27, No. 10, pp. 325-330 (Oct. 1, 2014).

Knudsen, Lotte Bjerre, "Glucagon-like Peptide-1: The Basis of a New Class of Treatment for Type 2 Diabetes", Journal of Medicinal Chemistry, vol. 47, No. 17, pp. 4128-4134 (2004).
Ljung et al., "40K glycoPEGylated, recombinant FVIIa: 3-month, double-blind, randomized trial of safety, pharmacokinetics and preliminary efficacy in hemophilia patients with inhibitors", Journal of Thrombosis and Haemostasis, vol. 11, pp. 1260-1268 (2013).
Luo et al., "Flexibility between the Protease and Helicase Domains of the Dengue Virus NS3 Protein Conferred by the Linker Region and Its Functional Implications", The Journal of Biological Chemistry, vol. 285, No. 24, pp. 18817-18827 (2010).
Maeda et al., Engineering of functional chimeric protein G-Vargula Luciferase, Analytical biochemistry, vol. 249, No. 2, pp. 147-152 (1997).
Micanovic et al., "Different Roles of N- and C-Termini in the Functional Activity of FGF21" Journal of cellular physiology, vol. 219, pp. 227-234 (2009).
Moore et al., "Particular fibroblast growth factors function as metabolic hormones and act through a certain signaling cascade design to control specific states of homeostasis", Science, vol. 316, pp. 1436-1438 (2007).
Neidigh et al., "Exendin-4 and Glucagon-like-peptide-1: NMR Structural Comparisons in the Solution and Micelle-Associated States", Biochemistry 2001, 40, 13188-13200 (2001).
Orlando M., Modification of proteins and low molecular weight substance with hydroxyethyl starch (HES), Inauguraldissertation, Giesen, 2003, p. 166, line 15.
Pedersen et al., "Autoactivation of Human Recombinant Coagulation Factor VII", Biochemistry, vol. 28, pp. 9331-9336 (1989).
Tang et al., "Selection of Linkers for a Catalytic Single-chain Antibody Using Phage Display Technology", The Journal of Biological Chemistry, vol. 271, No. 26, pp. 15682-15686 (1996).
Uchida et al., "Analysis of binding properties between 20 kDa human growth hormone (hGH) and hGH receptor (hGHR): the binding affinity for hGHR extracellular domain and mode of receptor dimerization", Journal of Molecular Endocrinology, vol. 23, pp. 347-353 (1999).
Weimer et al., "Prolonged in-vivo half-life of factor VIIa by fusion to albumin", Thromb Haemost, vol. 99, pp. 659-667 (2008).
Wu et al., "Separating mitogenic and metabolic activities of fibroblast growth factor 19 (FGF19)", PNAS, vol. 107, No. 32, pp. 14158-14163 (2010).
Xu et al., "Acute glucose-lowering and insulin-sensitizing action of FGF21 in insulin-resistant mouse models—association with liver and adipose tissue effects", Am J Physiol Endocrinol Metab, vol. 297, pp. E1105-E1114 (2009).
Xu et al., "Fibroblast Growth Factor 21 Reverse Hepatic Steatosis, Increases Energy Expenditure, and Improves Insulin Sensitivity in Diet-Induced Obese Mice", Diabetes, vol. 58, pp. 250-259 (2009).
Yie et al., "FGF21 N- and C-termini play different roles in receptor interaction and activation", FEBS Letters, vol. 583, pp. 19-24 (2009).
International Preliminary Report on Patentability and Written Opinion for Application No. PCT/CN2016/106011 dated Feb. 19, 2019.
International Preliminary Report on Patentability and Written Opinion for Application No. PCT/CN2017/079871 dated Feb. 19, 2019.
Restriction Requirement for U.S. Appl. No. 16/326,412 dated Jan. 8, 2020,.
Non-Final Office Action for U.S. Appl. No. 16/326,412 dated May 13, 2020.
European Office Action for Application No. 16913393.1 dated Jun. 17, 2020.
Chinese Office Action for Application No. 201910687158.3 dated Jul. 1, 2020.
Russian Office Action for Application No. 2019135518/10(070134) dated Jul. 2, 2020.
Canadian Office Action for Application No. 3059662 dated Oct. 6, 2020.
Final Office Action for U.S. Appl. No. 16/326,412 dated Oct. 27, 2020.
Canadian Office Action for Application No. 3059994 dated Oct. 28, 2020.

(56) References Cited

OTHER PUBLICATIONS

Japanese Office Action for Application No. 2019-530527 dated Nov. 24, 2020.
Advisory Action for U.S. Appl. No. 16/326,412 dated Dec. 7, 2020.
Korean Office Action for Application No. 20197007918 dated Jan. 7, 2021.
Final Office Action for U.S. Appl. No. 16/604,081 dated Jan. 28, 2021.
Extended European Search Report for Application No. 17840761.5 dated Jan. 29, 2021.
Non-Final Office Action for U.S. Appl. No. 16/326,412 dated Feb. 16, 2021.
Non-Final Office Action for U.S. Appl. No. 16/604,081 dated May 25, 2021.
Notice of Allowance for U.S. Appl. No. 16/326,412 dated May 27, 2021.
Li et al., "Design of Linker Peptides and Its Application in Fusion Protein," Journal of Food Science and Biotechnology, vol. 34, No. 11, pp. 1121-1127 (Dec. 14, 2015).
Li et al., "Construction of a linker library with widely controllable flexibility for fusion protein design", Appl. Microbiol Biotechnology, vol. 100, pp. 215-225, (Sep. 22, 2015).
Lin et al., "Fibroblast Growth Factor 21 Prevents Atherosclerosis by Suppression of Hepatic Sterol Regulatory Element-Binding Protein-2 and Induction of Adiponectin in Mice", Circulation, vol. 131, pp. 1861-1871, (Mar. 20, 2015).
McCue et al., "Manufacturing process used to produce long-acting recombinant factor VIII Fc fusion protein," Biologicals, vol. 43, pp. 213-219 (Jun. 17, 2015).
Petit et al., "GLP-1 receptor agonist in NAFLD", Diabetes & Metabolism, vol. 43, pp. 2S28-2S33, (Mar. 3, 2017).
Radaelli et al., "NAFLD/NASH in patients with type 2 diabetes and related treatment options", Journal of Endocrinological Investigation, vol. 41, pp. 509-521, (Nov. 30, 2017).
Salas et al., "Enhanced Pharmacokinetics of Factor VIIa as a Monomeric Fc Fusion", Thrombisis Research, vol. 135, pp. 970-976, (Jan. 3, 2015).
Non-Final Office Action for U.S. Appl. No. 16/604,801 dated Oct. 15, 2021.
Canadian Office Action for Application No. 3059994 dated Sep. 1, 2021.
Canadian Office Action for Application No. 3059662 dated Sep. 1, 2021.
British Office Action for Application No. 1903581 dated Aug. 2, 2021.

\* cited by examiner

```
  1                    M  Q  I  E  L  S  T  C  F  F  L  C  L  L  R  F
  1 actagccgccaccATGCAGATCGAACTGTCAACTTGTTTCTTCCTGTGCCTGCTGAGAT
 17    C  F  S  A  T  R  R  Y  Y  L  G  A  V  E  L  S  W  D  Y  M
 61 TTTGCTTTTCCGCCACTCGTCGTTACTACCTAGGAGCCGTGGAACTGAGCTGGGATTACA
 37    Q  S  D  L  G  E  L  P  V  D  A  R  F  P  P  R  V  P  K  S
121 TGCAGTCTGACCTGGGAGAGCTGCCAGTGGACGCTAGATTTCCCCCTCGCGTGCCTAAGA
 57    F  P  F  N  T  S  V  V  Y  K  K  T  L  F  V  E  F  T  D  H
181 GTTTCCCCTTCAACACCTCAGTGGTCTATAAGAAAACACTGTTCGTGGAGTTTACTGATC
 77    L  F  N  I  A  K  P  R  P  P  W  M  G  L  L  G  P  T  I  Q
241 ACCTGTTCAACATCGCCAAGCCAAGACCACCCTGGATGGGACTGCTGGGACCTACAATCC
 97    A  E  V  Y  D  T  V  V  I  T  L  K  N  M  A  S  H  P  V  S
301 AGGCTGAGGTGTACGACACTGTGGTCATTACCCTGAAAAACATGGCAAGTCACCCAGTGT
117    L  H  A  V  G  V  S  Y  W  K  A  S  E  G  A  E  Y  D  D  Q
361 CACTGCATGCCGTCGGGGTGTCATACTGGAAGGCTTCCGAAGGTGCAGAGTATGACGATC
137    T  S  Q  R  E  K  E  D  D  K  V  F  P  G  G  S  H  T  Y  V
421 AGACCTCTCAGCGCGAAAAGAGGACGATAAGGTGTTTCCCGGCGGAAGCCATACATACG
157    W  Q  V  L  K  E  N  G  P  M  A  S  D  P  L  C  L  T  Y  S
481 TCTGGCAGGTGCTGAAGGAGAATGGCCCCATGGCCAGCGACCCTCTGTGCCTGACCTACT
177    Y  L  S  H  V  D  L  V  K  D  L  N  S  G  L  I  G  A  L  L
541 CATATCTGTCCCACGTGGACCTGGTGAAGGATCTGAACAGCGGGCTGATCGGTGCACTGC
197    V  C  R  E  G  S  L  A  K  E  K  T  Q  T  L  H  K  F  I  L
601 TGGTGTGTAGAGAAGGCTCTCTGGCCAAGGAGAAAACTCAGACCCTGCATAAGTTCATTC
217    L  F  A  V  F  D  E  G  K  S  W  H  S  E  T  K  N  S  L  M
661 TGCTGTTCGCCGTGTTTGACGAAGGAAAAAGCTGGCACTCTGAGACTAAGAACTCCCTGA
237    Q  D  R  D  A  A  S  A  R  A  W  P  K  M  H  T  V  N  G  Y
721 TGCAGGACAGGGATGCAGCAAGCGCACGAGCTTGGCCCAAAATGCATACCGTCAACGGCT
257    V  N  R  S  L  P  G  L  I  G  C  H  R  K  S  V  Y  W  H  V
781 ACGTGAATCGAAGTCTGCCTGGCCTGATCGGATGCCACCGTAAGTCCGTCTATTGGCATG
277    I  G  M  G  T  T  P  E  V  H  S  I  F  L  E  G  H  T  F  L
841 TGATCGGGATGGGCACCACACCCGAAGTCCACAGCATTTTCCTGGAGGGTCATACCTTTC
297    V  R  N  H  R  Q  A  S  L  E  I  S  P  I  T  F  L  T  A  Q
901 TGGTGAGAAACCACCGCCAGGCATCCCTGGAGATCAGCCCTATTACTTTCCTGACCGCCC
317    T  L  L  M  D  L  G  Q  F  L  L  F  C  H  I  S  S  H  Q  H
961 AGACACTGCTGATGGATCTGGGCCAGTTCCTGCTGTTTTGCCACATCTCCAGCCACCAGC
337    D  G  M  E  A  Y  V  K  V  D  S  C  P  E  E  P  Q  L  R  M
1021 ATGATGGAATGGAGGCATACGTCAAAGTGGACTCTTGTCCTGAGGAACCACAACTGAGGA
```

Figure 1

```
357        K  N  N  E  E  A  E  D  Y  D  D  D  L  T  D  S  E  M  D  V
1081 TGAAGAACAATGAGGAAGCCGAAGACTATGACGATGACCTGACAGACTCCGAGATGGATG
377        V  R  F  D  D  N  S  P  S  F  I  Q  I  R  S  V  A  K  K
1141 TGGTCCGCTTCGATGACGATAACTCCCCTAGCTTTATCCAGATTCGAAGCGTCGCCAAGA
397        H  P  K  T  W  V  H  Y  I  A  A  E  E  D  W  D  Y  A  P
1201 AACACCCAAAGACTTGGGTGCATTACATCGCAGCCGAGGAAGAGGACTGGGATTATGCTC
417        L  V  L  A  P  D  D  R  S  Y  K  S  Q  Y  L  N  N  G  P  Q
1261 CACTGGTGCTGGCACCCGATGATCGGAGTTACAAATCACAGTATCTGAACAATGGGCCTC
437        R  I  G  R  K  Y  K  K  V  R  F  M  A  Y  T  D  E  T  F  K
1321 AGCGAATTGGTCGTAAGTACAAGAAAGTGCGATTCATGGCCTATACTGATGAAACCTTTA
457        T  R  E  A  I  Q  H  E  S  G  I  L  G  P  L  L  Y  G  E  V
1381 AGACACGTGAAGCTATCCAGCACGAGTCTGGGATTCTGGGTCCACTGCTGTACGGCGAAG
477        G  D  T  L  L  I  I  F  K  N  Q  A  S  R  P  Y  N  I  Y  P
1441 TGGGAGACACACTGCTGATCATTTTTAAGAACCAGGCAAGCAGACCTTACAATATCTATC
497        H  G  I  T  D  V  R  P  L  Y  S  R  R  L  P  K  G  V  K  H
1501 CACATGGAATTACTGATGTCCGGCCTCTGTACTCTAGGCGGCTGCCAAAGGGGGTGAAAC
517        L  K  D  F  P  I  L  P  G  E  I  F  K  Y  K  W  T  V  T  V
1561 ACCTGAAGGACTTCCCCATCCTGCCTGGTGAAATTTTTAAGTACAAGTGGACAGTCACTG
537        E  D  G  P  T  K  S  D  P  R  C  L  T  R  Y  Y  S  S  F  V
1621 TGGAGGATGGGCCAACAAAGTCTGACCCTCGATGCCTGACTCGTTACTATTCTAGTTTCG
557        N  M  E  R  D  L  A  S  G  L  I  G  P  L  L  I  C  Y  K  E
1681 TGAATATGGAAAGAGACCTGGCCTCCGGGCTGATCGGTCCTCTGCTGATTTGTTACAAAG
577        S  V  D  Q  R  G  N  Q  I  M  S  D  K  R  N  V  I  L  F  S
1741 AGTCTGTGGATCAGAGGGGCAACCAGATCATGAGTGACAAGCGGAATGTCATTCTGTTCA
597        V  F  D  E  N  R  S  W  Y  L  T  E  N  I  Q  R  F  L  P  N
1801 GCGTGTTTGACGAAAACAGGTCTTGGTATCTGACCGAGAACATCCAGCGGTTCCTGCCAA
617        P  A  G  V  Q  L  E  D  P  E  F  Q  A  S  N  I  M  H  S  I
1861 ATCCCGCAGGCGTGCAGCTTGAAGATCCAGAGTTTCAGGCCAGCAACATCATGCATTCTA
637        N  G  Y  V  F  D  S  L  Q  L  S  V  C  L  H  E  V  A  Y  W
1921 TTAATGGATACGTGTTCGACTCTCTGCAGTTGAGTGTCTGTCTGCACGAGGTGGCCTACT
657        Y  I  L  S  I  G  A  Q  T  D  F  L  S  V  F  F  S  G  Y  T
1981 GGTATATCCTGTCTATTGGCGCTCAGACTGATTTCCTGTCAGTGTTCTTTTCCGGATACA
677        F  K  H  K  M  V  Y  E  D  T  L  T  L  F  P  F  S  G  E  T
2041 CCTTTAAGCATAAAATGGTGTATGAGGACACCCTGACACTGTTCCCCTTTAGTGGCGAAA
697        V  F  M  S  M  E  N  P  G  L  W  I  L  G  C  H  N  S  D  F
2101 CCGTGTTTATGTCAATGGAGAATCCTGGCCTGTGGATTCTGGGATGCCACAACTCCGATT
717        R  N  R  G  M  T  A  L  L  K  V  S  S  C  D  K  N  T  G  D
2161 TCAGAAATCGCGGGATGACCGCTCTGCTGAAAGTGTCATCCTGTGACAAGAACACTGGTG
737        Y  Y  E  D  S  Y  E  D  I  S  A  Y  L  L  S  K  N  N  A  I
```

```
2221 ACTACTATGAAGATAGTTACGAGGACATCTCAGCTTATCTGCTGTCCAAAAACAATGCAA
 757    E  P  R  S  F  S  Q  N  P  P  V  L  K  R  H  Q  R  E  I  T
2281 TTGAACCACGATCTTTTAGTCAGAATCCTCCAGTGCTGAAGAGGCACCAGCGGGAGATCA
 777    R  T  T  L  Q  S  D  Q  E  E  I  D  Y  D  D  T  I  S  V  E
2341 CAAGGACTACCCTGCAGAGTGATCAGGAAGAGATCGACTACGACGATACTATTTCCGTGG
 797    M  K  K  E  D  F  D  I  Y  D  E  D  E  N  Q  S  P  R  S  F
2401 AAATGAAGAAAGAGGACTTCGACATCTATGACGAAGATGAGAACCAGTCCCCCAGGAGCT
 817    Q  K  K  T  R  H  Y  F  I  A  A  V  E  R  L  W  D  Y  G  M
2461 TCCAGAAGAAAACCCGTCATTACTTTATTGCTGCAGTGGAGCGCCTGTGGGATTATGGCA
 837    S  S  S  P  H  V  L  R  N  R  A  Q  S  G  S  V  P  Q  F  K
2521 TGAGCTCTAGTCCACACGTCCTGCGAAATCGTGCCCAGTCAGGCTCCGTGCCCCAGTTCA
 857    K  V  V  F  Q  E  F  T  D  G  S  F  T  Q  P  L  Y  R  G  E
2581 AGAAAGTGGTCTTCCAGGAGTTTACAGACGGCTCCTTTACTCAGCCACTGTACAGAGGAG
 877    L  N  E  H  L  G  L  L  G  P  Y  I  R  A  E  V  E  D  N  I
2641 AACTGAACGAGCATCTGGGCCTGCTGGGACCCTATATCCGCGCCGAAGTCGAGGATAACA
 897    M  V  T  F  R  N  Q  A  S  R  P  Y  S  F  Y  S  S  L  I  S
2701 TTATGGTGACCTTCAGAAATCAGGCCAGCCGCCCCTACTCTTTTTATTCATCCCTGATCA
 917    Y  E  E  D  Q  R  Q  G  A  E  P  R  K  N  F  V  K  P  N  E
2761 GCTACGAAGAGGACCAGAGACAGGGCGCTGAACCCCGCAAAAACTTCGTGAAGCCTAATG
 937    T  K  T  Y  F  W  K  V  Q  H  H  M  A  P  T  K  D  E  F  D
2821 AGACTAAAACCTACTTTTGGAAGGTGCAGCACCACATGGCACCTACAAAAGACGAGTTCG
 957    C  K  A  W  A  Y  F  S  D  V  D  L  E  K  D  V  H  S  G  L
2881 ATTGCAAGGCATGGGCCTATTTTTCAGACGTCGATCTGGAGAAGGACGTGCATTCTGGGC
 977    I  G  P  L  L  V  C  H  T  N  T  L  N  P  A  H  G  R  Q  V
2941 TGATCGGTCCCCTGCTGGTGTGTCATACAAACACTCTGAATCCTGCTCACGGCAGGCAGG
 997    T  V  Q  E  F  A  L  F  F  T  I  F  D  E  T  K  S  W  Y  F
3001 TCACCGTGCAGGAATTTGCACTGTTCTTTACCATCTTTGATGAGACAAAGTCTTGGTACT
1017    T  E  N  M  E  R  N  C  R  A  P  C  N  I  Q  M  E  D  P  T
3061 TTACAGAAAACATGGAGAGAAATTGCCGCGCTCCTTGTAATATTCAGATGGAAGACCCAA
1037    F  K  E  N  Y  R  F  H  A  I  N  G  Y  I  M  D  T  L  P  G
3121 CTTTCAAGGAGAACTATCGGTTTCATGCAATCAATGGCTATATTATGGATACCCTGCCTG
1057    L  V  M  A  Q  D  Q  R  I  R  W  Y  L  L  S  M  G  S  N  E
3181 GACTGGTCATGGCCCAGGACCAGAGGATTCGGTGGTATCTGCTGTCTATGGGAGTAACG
1077    N  I  H  S  I  H  F  S  G  H  V  F  T  V  R  K  K  E  E  Y
3241 AGAATATCCACAGTATTCATTTCTCAGGTCACGTCTTTACCGTGAGGAAGAAAGAAGAGT
1097    K  M  A  L  Y  N  L  Y  P  G  V  F  E  T  V  E  M  L  P  S
3301 ATAAAATGGCCCTGTACAACCTGTATCCAGGCGTCTTCGAAACAGTGGAGATGCTGCCCT
1117    K  A  G  I  W  R  V  E  C  L  I  G  E  H  L  H  A  G  M  S
3361 CCAAGGCTGGAATCTGGCGGGTGGAATGCCTGATTGGGGAGCACCTGCATGCAGGCATGT
```

Figure 1 cont'd

```
1137    T  L  F  L  V  Y  S  N  K  C  Q  T  P  L  G  M  A  S  G  H
3421  CCACACTGTTTCTGGTGTACAGCAATAAGTGTCAGACTCCACTGGGGATGGCCAGCGGTC
1157    I  R  D  F  Q  I  T  A  S  G  Q  Y  G  Q  W  A  P  K  L  A
3481  ATATCCGGGATTTCCAGATTACCGCTTCTGGCCAGTACGGACAGTGGGCTCCCAAGCTGG
1177    R  L  H  Y  S  G  S  I  N  A  W  S  T  K  E  P  F  S  W  I
3541  CTAGACTGCACTATAGCGGCTCTATCAACGCCTGGTCCACTAAAGAGCCCTTCTCCTGGA
1197    K  V  D  L  L  A  P  M  I  I  H  G  I  K  T  Q  G  A  R  Q
3601  TTAAGGTGGACCTGCTGGCTCCATGATCATTCATGGGATCAAAACCCAGGGTGCACGCC
1217    K  F  S  S  L  Y  I  S  Q  F  I  I  M  Y  S  L  D  G  K  K
3661  AGAAGTTCAGCTCTCTGTACATCTCTCAGTTTATCATCATGTACAGTCTGGATGGAAAGA
1237    W  Q  T  Y  R  G  N  S  T  G  T  L  M  V  F  G  N  V  D
3721  AATGGCAGACCTACCGAGGCAATTCCACCGGAACACTGATGGTCTTCTTTGGCAACGTGG
1257    S  S  G  I  K  H  N  I  F  N  P  P  I  I  A  R  Y  I  R  L
3781  ACAGTTCAGGAATCAAGCACAACATTTTCAATCCCCCTATCATTGCTCGATACATCCGTC
1277    H  P  T  H  Y  S  I  R  S  T  L  R  M  E  L  M  G  C  D  L
3841  TGCACCCTACCCATTATTCAATTAGGTCCACACTGCGGATGGAACTGATGGGGTGCGATC
1297    N  S  C  S  M  P  L  G  M  E  S  K  A  I  S  D  A  Q  I  T
3901  TGAACAGTTGTTCAATGCCACTGGGTATGGAGTCCAAGGCAATCAGCGACGCCCAGATTA
1317    A  S  S  Y  F  T  N  M  F  A  T  W  S  P  S  K  A  R  L  H
3961  CCGCTTCCAGCTACTTCACTAATATGTTTGCCACCTGGTCCCCCAGCAAAGCTAGGCTGC
1337    L  Q  G  R  S  N  A  W  R  P  Q  V  N  N  P  K  E  W  L  Q
4021  ATCTGCAGGGCCGAAGCAACGCCTGGCGTCCACAGGTCAACAATCCCAAGGAGTGGCTGC
1357    V  D  F  Q  K  T  M  K  V  T  G  V  T  T  Q  G  V  K  S  L
4081  AGGTGGATTTTCAGAAAACAATGAAGGTCACTGGCGTGACAACTCAGGGAGTCAAATCTC
1377    L  T  S  M  Y  V  K  E  F  L  I  S  S  S  Q  D  G  H  Q  W
4141  TGCTGACAAGTATGTACGTGAAGGAGTTCCTGATCTCTAGTTCACAGGACGGACACCAGT
1397    T  L  F  F  Q  N  G  K  V  K  V  F  Q  G  N  Q  D  S  F  T
4201  GGACTCTGTTCTTTCAGAACGGGAAGGTCAAAGTGTTCCAGGGTAATCAGGATTCCTTCA
1417    P  V  V  N  S  L  D  P  P  L  L  T  R  Y  L  R  I  H  P  Q
4261  CCCCTGTGGTCAACTCTCTAGACCCACCCCTGCTGACCAGGTATCTGCGAATCCACCCAC
1437    S  W  V  H  Q  I  A  L  R  M  E  V  L  G  C  E  A  Q  D  L
4321  AGAGCTGGGTCCATCAGATTGCTCTGAGAATGGAAGTGCTGGGGTGCGAGGCACAGGATC
1457    Y  G  S  G  G  G  S  G  G  G  S  G  G  G  S  G  G
4381  TGTATGGATCCGGTGGCGGTGGCTCCGGTGGAGGCGGAAGCGGCGGTGGAGGATCAGGCG
1477    G  G  S  G  G  G  S  S  S  S  K  A  P  P  P  S  L  P
4441  GTGGAGGTAGCGGCGGAGGCGGTAGCTCCAGCTCTAGTAAAGCTCCCCCTCCTTCCCTGC
1497    S  F  S  R  L  P  G  P  S  D  T  P  I  L  P  Q  V  E  C  P
4501  CCTCACCCTCAAGACTGCCTGGACCTTCCGACACTCCCATCCTGCCACAGGTGGAGTGCC
1517    P  C  P  A  P  P  V  A  G  P  S  V  F  L  F  P  P  K  P  K
```

```
4561  CTCCATGTCCAGCACCCCTGTCGCAGGTCCATCTGTGTTCCTGTTTCCACCCAAGCCTA
1537   D  Q  L  M  I  S  R  T  P  E  V  T  C  V  V  V  D  V  S  H
4621  AAGACCAGCTGATGATCTCCCGCACCCCAGAAGTCACCTGTGTGGTCGTGGATGTGAGCC
1557   E  D  P  E  V  Q  F  N  W  Y  V  D  G  V  E  V  H  N  A  K
4681  ATGAAGACCCCGAGGTCCAGTTCAATTGGTACGTGGATGGCGTCGAGGTGCACAACGCTA
1577   T  K  P  R  E  E  Q  F  N  S  T  F  R  V  V  S  V  L  T  V
4741  AGACAAAACCTAGAGAAGAGCAGTTCAACTCTACCTTTCGCGTCGTGAGTGTGCTGACAG
1597   V  H  Q  D  W  L  N  G  K  E  Y  K  C  K  V  S  N  K  G  L
4801  TCGTGCACCAGGACTGGCTGAATGGCAAGGAGTATAAGTGCAAAGTGAGCAACAAAGGAC
1617   P  A  S  I  E  K  T  I  S  K  T  G  Q  P  R  E  P  Q  V
4861  TGCCTGCCTCAATCGAAAAGACTATTTCCAAGACCAAAGGACAGCCAAGAGAGCCCCAGG
1637   Y  T  L  P  P  S  R  E  E  M  T  K  N  Q  V  S  L  T  C  L
4921  TGTACACCCTGCCTCCAAGCCGCGAAGAGATGACTAAAAATCAGGTCTCTCTGACCTGTC
1657   V  K  G  F  Y  P  S  D  I  A  V  E  W  E  S  N  G  Q  P  E
4981  TGGTGAAGGGGTTTTATCCTAGTGATATCGCCGTGGAATGGGAGTCAAACGGTCAGCCAG
1677   N  N  Y  K  T  T  P  P  M  L  D  S  D  G  S  F  F  L  Y  S
5041  AGAACAATTACAAGACCACACCCCCTATGCTGGACAGCGATGGGTCTTTCTTTCTGTATA
1697   K  L  T  V  D  K  S  R  W  Q  Q  G  N  V  F  S  C  S  V  L
5101  GCAAACTGACAGTGGACAAGTCTCGGTGGCAGCAGGGTAACGTCTTCTCTTGCAGTGTGC
1717   H  E  A  L  H  N  H  Y  T  Q  K  S  L  S  L  S  P  G  K  *
5161  TGCACGAAGCACTGCACAATCATTACACCCAGAAGTCACTGTCACTGAGCCCAGGAAAAT
5221  GAatccaacgggctgatgctgcaccaactgtatccgaattc
```

Figure 1 cont'd

SEQUENCE LISTING

<160> NUMBER OF SEQ ID NOS: 21

<210> SEQ ID NO 1
<211> LENGTH: 1438
<212> TYPE: PRT
<213> ORGANISM: Homo sapiens

<400> SEQUENCE: 1

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190
```

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

-continued

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Val Leu Lys Arg His
                740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
        770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
                820                 825                 830

Val Pro Gln Phe Lys Lys Val Phe Gln Glu Phe Thr Asp Gly Ser
        835                 840                 845

Phe Thr Gln Pro Leu Tyr Arg Gly Glu Leu Asn Glu His Leu Gly Leu
        850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
                980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu

```
            1025                1030                1035

Val Met Ala Gln Asp Gln Arg Ile Arg Trp Tyr Leu Leu Ser Met
        1040                1045                1050

Gly Ser Asn Glu Asn Ile His Ser Ile His Phe Ser Gly His Val
        1055                1060                1065

Phe Thr Val Arg Lys Lys Glu Glu Tyr Lys Met Ala Leu Tyr Asn
        1070                1075                1080

Leu Tyr Pro Gly Val Phe Glu Thr Val Glu Met Leu Pro Ser Lys
        1085                1090                1095

Ala Gly Ile Trp Arg Val Glu Cys Leu Ile Gly Glu His Leu His
        1100                1105                1110

Ala Gly Met Ser Thr Leu Phe Leu Val Tyr Ser Asn Lys Cys Gln
        1115                1120                1125

Thr Pro Leu Gly Met Ala Ser Gly His Ile Arg Asp Phe Gln Ile
        1130                1135                1140

Thr Ala Ser Gly Gln Tyr Gly Gln Trp Ala Pro Lys Leu Ala Arg
        1145                1150                1155

Leu His Tyr Ser Gly Ser Ile Asn Ala Trp Ser Thr Lys Glu Pro
        1160                1165                1170

Phe Ser Trp Ile Lys Val Asp Leu Leu Ala Pro Met Ile Ile His
        1175                1180                1185

Gly Ile Lys Thr Gln Gly Ala Arg Gln Lys Phe Ser Ser Leu Tyr
        1190                1195                1200

Ile Ser Gln Phe Ile Ile Met Tyr Ser Leu Asp Gly Lys Lys Trp
        1205                1210                1215

Gln Thr Tyr Arg Gly Asn Ser Thr Gly Thr Leu Met Val Phe Phe
        1220                1225                1230

Gly Asn Val Asp Ser Ser Gly Ile Lys His Asn Ile Phe Asn Pro
        1235                1240                1245

Pro Ile Ile Ala Arg Tyr Ile Arg Leu His Pro Thr His Tyr Ser
        1250                1255                1260

Ile Arg Ser Thr Leu Arg Met Glu Leu Met Gly Cys Asp Leu Asn
        1265                1270                1275

Ser Cys Ser Met Pro Leu Gly Met Glu Ser Lys Ala Ile Ser Asp
        1280                1285                1290

Ala Gln Ile Thr Ala Ser Ser Tyr Phe Thr Asn Met Phe Ala Thr
        1295                1300                1305

Trp Ser Pro Ser Lys Ala Arg Leu His Leu Gln Gly Arg Ser Asn
        1310                1315                1320

Ala Trp Arg Pro Gln Val Asn Asn Pro Lys Glu Trp Leu Gln Val
        1325                1330                1335

Asp Phe Gln Lys Thr Met Lys Val Thr Gly Val Thr Thr Gln Gly
        1340                1345                1350

Val Lys Ser Leu Leu Thr Ser Met Tyr Val Lys Glu Phe Leu Ile
        1355                1360                1365

Ser Ser Ser Gln Asp Gly His Gln Trp Thr Leu Phe Phe Gln Asn
        1370                1375                1380

Gly Lys Val Lys Val Phe Gln Gly Asn Gln Asp Ser Phe Thr Pro
        1385                1390                1395

Val Val Asn Ser Leu Asp Pro Pro Leu Leu Thr Arg Tyr Leu Arg
        1400                1405                1410

Ile His Pro Gln Ser Trp Val His Gln Ile Ala Leu Arg Met Glu
        1415                1420                1425
```

Val Leu Gly Cys Glu Ala Gln Asp Leu Tyr
    1430                1435

<210> SEQ ID NO 2
<211> LENGTH: 16
<212> TYPE: PRT
<213> ORGANISM: Artificial sequence
<220> FEATURE:
<223> OTHER INFORMATION: L1 amino acid sequence

<400> SEQUENCE: 2

Gly Ser Gly Gly Gly Ser Gly Gly Gly Ser Gly Gly Gly Gly Ser
1               5                   10                  15

<210> SEQ ID NO 3
<211> LENGTH: 27
<212> TYPE: PRT
<213> ORGANISM: Artificial sequence
<220> FEATURE:
<223> OTHER INFORMATION: L2 amino acid sequence

<400> SEQUENCE: 3

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 4
<211> LENGTH: 20
<212> TYPE: PRT
<213> ORGANISM: Artificial sequence
<220> FEATURE:
<223> OTHER INFORMATION: L3 amino acid sequence

<400> SEQUENCE: 4

Gly Gly Gly Gly Ser Gly Gly Gly Ser Gly Gly Gly Gly Ser Gly
1               5                   10                  15

Gly Gly Gly Ser
            20

<210> SEQ ID NO 5
<211> LENGTH: 37
<212> TYPE: PRT
<213> ORGANISM: Artificial sequence
<220> FEATURE:
<223> OTHER INFORMATION: L4 amino acid sequence

<400> SEQUENCE: 5

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser
        35

<210> SEQ ID NO 6
<211> LENGTH: 20
<212> TYPE: PRT
<213> ORGANISM: Artificial sequence
<220> FEATURE:
<223> OTHER INFORMATION: L5 amino acid sequence

<400> SEQUENCE: 6

Gly Gly Gly Ser Gly Gly Gly Ser Gly Gly Gly Ser Gly Gly Gly Ser

-continued

```
                1               5                  10                 15
Gly Gly Gly Ser
            20

<210> SEQ ID NO 7
<211> LENGTH: 33
<212> TYPE: PRT
<213> ORGANISM: Homo sapiens

<400> SEQUENCE: 7

Pro Arg Phe Gln Asp Ser Ser Ser Lys Ala Pro Pro Ser Leu
1               5                   10                  15

Pro Ser Pro Ser Arg Leu Pro Gly Pro Ser Asp Thr Pro Ile Leu Pro
            20                  25                  30

Gln

<210> SEQ ID NO 8
<211> LENGTH: 28
<212> TYPE: PRT
<213> ORGANISM: Homo sapiens

<400> SEQUENCE: 8

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 9
<211> LENGTH: 10
<212> TYPE: PRT
<213> ORGANISM: Homo sapiens

<400> SEQUENCE: 9

Ser Ser Ser Ser Lys Ala Pro Pro Pro Ser
1               5                   10

<210> SEQ ID NO 10
<211> LENGTH: 14
<212> TYPE: PRT
<213> ORGANISM: Homo sapiens

<400> SEQUENCE: 10

Ser Arg Leu Pro Gly Pro Ser Asp Thr Pro Ile Leu Pro Gln
1               5                   10

<210> SEQ ID NO 11
<211> LENGTH: 227
<212> TYPE: PRT
<213> ORGANISM: Artificial sequence
<220> FEATURE:
<223> OTHER INFORMATION: vFcgamma1 amino acid sequence

<400> SEQUENCE: 11

Asp Lys Thr His Thr Cys Pro Pro Cys Pro Ala Pro Glu Val Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 12
<211> LENGTH: 223
<212> TYPE: PRT
<213> ORGANISM: Artificial sequence
<220> FEATURE:
<223> OTHER INFORMATION: vFcgamma2-1 amino acid sequence

<400> SEQUENCE: 12

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

```
Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
    210                 215                 220

<210> SEQ ID NO 13
<211> LENGTH: 223
<212> TYPE: PRT
<213> ORGANISM: Artificial sequence
<220> FEATURE:
<223> OTHER INFORMATION: vFcgamma2-2 amino acid sequence

<400> SEQUENCE: 13

Val Glu Cys Pro Pro Cys Pro Ala Pro Val Ala Gly Pro Ser Val
1               5                   10                  15

Phe Leu Phe Pro Pro Lys Pro Lys Asp Gln Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
            195                 200                 205

His Asn His Tyr Thr Gln Lys Ser Leu Ser Leu Ser Pro Gly Lys
    210                 215                 220

<210> SEQ ID NO 14
<211> LENGTH: 223
<212> TYPE: PRT
<213> ORGANISM: Artificial sequence
<220> FEATURE:
<223> OTHER INFORMATION: vFcgamma2-3 amino acid sequence

<400> SEQUENCE: 14

Val Glu Cys Pro Pro Cys Pro Ala Pro Val Ala Gly Pro Ser Val
1               5                   10                  15

Phe Leu Phe Pro Pro Lys Pro Lys Asp Gln Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
    50                  55                  60
```

```
Thr Lys Pro Arg Glu Glu Gln Phe Asn Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220

<210> SEQ ID NO 15
<211> LENGTH: 229
<212> TYPE: PRT
<213> ORGANISM: Artificial sequence
<220> FEATURE:
<223> OTHER INFORMATION: vFcgamma4 amino acid sequence

<400> SEQUENCE: 15

Glu Ser Lys Tyr Gly Pro Pro Cys Pro Pro Cys Pro Ala Pro Glu Phe
1               5                  10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205
```

Val Met His Glu Ala Leu His Asn His Tyr Thr Gln Lys Ser Leu Ser
    210                 215                 220

Leu Ser Leu Gly Lys
225

<210> SEQ ID NO 16
<211> LENGTH: 1716
<212> TYPE: PRT
<213> ORGANISM: Artificial sequence
<220> FEATURE:
<223> OTHER INFORMATION: FP-B amino acid sequence

<400> SEQUENCE: 16

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

```
Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750
```

```
Gln Arg Glu Ile Thr Arg Thr Thr Leu Gln Ser Asp Gln Glu Ile
            755                 760                 765
Asp Tyr Asp Asp Thr Ile Ser Val Glu Met Lys Lys Glu Asp Phe Asp
        770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Pro His Val Leu Arg Asn Arg Ala Gln Ser Gly Ser
            820                 825                 830
Val Pro Gln Phe Lys Lys Val Val Phe Gln Glu Phe Thr Asp Gly Ser
        835                 840                 845
Phe Thr Gln Pro Leu Tyr Arg Gly Glu Leu Asn Glu His Leu Gly Leu
    850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
            900                 905                 910
Val Lys Pro Asn Glu Thr Lys Thr Tyr Phe Trp Lys Val Gln His His
        915                 920                 925
Met Ala Pro Thr Lys Asp Glu Phe Asp Cys Lys Ala Trp Ala Tyr Phe
    930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
Val Thr Val Gln Glu Phe Ala Leu Phe Phe Thr Ile Phe Asp Glu Thr
            980                 985                 990
Lys Ser Trp Tyr Phe Thr Glu Asn Met Glu Arg Asn Cys Arg Ala Pro
        995                 1000                1005
Cys Asn Ile Gln Met Glu Asp Pro Thr Phe Lys Glu Asn Tyr Arg
    1010                1015                1020
Phe His Ala Ile Asn Gly Tyr Ile Met Asp Thr Leu Pro Gly Leu
    1025                1030                1035
Val Met Ala Gln Asp Gln Arg Ile Arg Trp Tyr Leu Leu Ser Met
    1040                1045                1050
Gly Ser Asn Glu Asn Ile His Ser Ile His Phe Ser Gly His Val
1055                1060                1065
Phe Thr Val Arg Lys Lys Glu Glu Tyr Lys Met Ala Leu Tyr Asn
    1070                1075                1080
Leu Tyr Pro Gly Val Phe Glu Thr Val Glu Met Leu Pro Ser Lys
    1085                1090                1095
Ala Gly Ile Trp Arg Val Glu Cys Leu Ile Gly Glu His Leu His
    1100                1105                1110
Ala Gly Met Ser Thr Leu Phe Leu Val Tyr Ser Asn Lys Cys Gln
    1115                1120                1125
Thr Pro Leu Gly Met Ala Ser Gly His Ile Arg Asp Phe Gln Ile
    1130                1135                1140
Thr Ala Ser Gly Gln Tyr Gly Gln Trp Ala Pro Lys Leu Ala Arg
    1145                1150                1155
Leu His Tyr Ser Gly Ser Ile Asn Ala Trp Ser Thr Lys Glu Pro
```

-continued

```
            1160                1165                1170
Phe Ser Trp Ile Lys Val Asp Leu Leu Ala Pro Met Ile Ile His
        1175                1180                1185
Gly Ile Lys Thr Gln Gly Ala Arg Gln Lys Phe Ser Ser Leu Tyr
        1190                1195                1200
Ile Ser Gln Phe Ile Ile Met Tyr Ser Leu Asp Gly Lys Lys Trp
        1205                1210                1215
Gln Thr Tyr Arg Gly Asn Ser Thr Gly Thr Leu Met Val Phe Phe
        1220                1225                1230
Gly Asn Val Asp Ser Ser Gly Ile Lys His Asn Ile Phe Asn Pro
        1235                1240                1245
Pro Ile Ile Ala Arg Tyr Ile Arg Leu His Pro Thr His Tyr Ser
        1250                1255                1260
Ile Arg Ser Thr Leu Arg Met Glu Leu Met Gly Cys Asp Leu Asn
        1265                1270                1275
Ser Cys Ser Met Pro Leu Gly Met Glu Ser Lys Ala Ile Ser Asp
        1280                1285                1290
Ala Gln Ile Thr Ala Ser Ser Tyr Phe Thr Asn Met Phe Ala Thr
        1295                1300                1305
Trp Ser Pro Ser Lys Ala Arg Leu His Leu Gln Gly Arg Ser Asn
        1310                1315                1320
Ala Trp Arg Pro Gln Val Asn Asn Pro Lys Glu Trp Leu Gln Val
        1325                1330                1335
Asp Phe Gln Lys Thr Met Lys Val Thr Gly Val Thr Thr Gln Gly
        1340                1345                1350
Val Lys Ser Leu Leu Thr Ser Met Tyr Val Lys Glu Phe Leu Ile
        1355                1360                1365
Ser Ser Ser Gln Asp Gly His Gln Trp Thr Leu Phe Phe Gln Asn
        1370                1375                1380
Gly Lys Val Lys Val Phe Gln Gly Asn Gln Asp Ser Phe Thr Pro
        1385                1390                1395
Val Val Asn Ser Leu Asp Pro Pro Leu Leu Thr Arg Tyr Leu Arg
        1400                1405                1410
Ile His Pro Gln Ser Trp Val His Gln Ile Ala Leu Arg Met Glu
        1415                1420                1425
Val Leu Gly Cys Glu Ala Gln Asp Leu Tyr Gly Ser Gly Gly Gly
        1430                1435                1440
Gly Ser Gly Gly Gly Gly Ser Gly Gly Gly Gly Ser Gly Gly Gly
        1445                1450                1455
Gly Ser Gly Gly Gly Gly Ser Ser Ser Ser Lys Ala Pro Pro
        1460                1465                1470
Pro Ser Leu Pro Ser Pro Ser Arg Leu Pro Gly Pro Ser Asp Thr
        1475                1480                1485
Pro Ile Leu Pro Gln Val Glu Cys Pro Pro Cys Pro Ala Pro Pro
        1490                1495                1500
Val Ala Gly Pro Ser Val Phe Leu Phe Pro Pro Lys Pro Lys Asp
        1505                1510                1515
Gln Leu Met Ile Ser Arg Thr Pro Glu Val Thr Cys Val Val Val
        1520                1525                1530
Asp Val Ser His Glu Asp Pro Glu Val Gln Phe Asn Trp Tyr Val
        1535                1540                1545
Asp Gly Val Glu Val His Asn Ala Lys Thr Lys Pro Arg Glu Glu
        1550                1555                1560
```

```
Gln Phe Asn Ser Thr Phe Arg Val Val Ser Val Leu Thr Val Val
    1565            1570                1575

His Gln Asp Trp Leu Asn Gly Lys Glu Tyr Lys Cys Lys Val Ser
    1580            1585                1590

Asn Lys Gly Leu Pro Ala Ser Ile Glu Lys Thr Ile Ser Lys Thr
    1595            1600                1605

Lys Gly Gln Pro Arg Glu Pro Gln Val Tyr Thr Leu Pro Pro Ser
    1610            1615                1620

Arg Glu Glu Met Thr Lys Asn Gln Val Ser Leu Thr Cys Leu Val
    1625            1630                1635

Lys Gly Phe Tyr Pro Ser Asp Ile Ala Val Glu Trp Glu Ser Asn
    1640            1645                1650

Gly Gln Pro Glu Asn Asn Tyr Lys Thr Thr Pro Pro Met Leu Asp
    1655            1660                1665

Ser Asp Gly Ser Phe Phe Leu Tyr Ser Lys Leu Thr Val Asp Lys
    1670            1675                1680

Ser Arg Trp Gln Gln Gly Asn Val Phe Ser Cys Ser Val Leu His
    1685            1690                1695

Glu Ala Leu His Asn His Tyr Thr Gln Lys Ser Leu Ser Leu Ser
    1700            1705                1710

Pro Gly Lys
    1715
```

<210> SEQ ID NO 17
<211> LENGTH: 5208
<212> TYPE: DNA
<213> ORGANISM: Artificial sequence
<220> FEATURE:
<223> OTHER INFORMATION: FP-B nucleotide sequence

<400> SEQUENCE: 17

```
atgcagatcg aactgtcaac ttgtttcttc ctgtgcctgc tgagattttg ctttttccgcc   60
actcgtcgtt actacctagg agccgtggaa ctgagctggg attacatgca gtctgacctg  120
ggagagctgc cagtggacgc tagatttccc cctcgcgtgc ctaagagttt ccccttcaac  180
acctcagtgg tctataagaa aacactgttc gtggagttta ctgatcacct gttcaacatc  240
gccaagccaa gaccaccctg gatgggactg ctgggaccta caatccaggc tgaggtgtac  300
gacactgtgg tcattaccct gaaaaacatg gcaagtcacc cagtgtcact gcatgccgtc  360
ggggtgtcat actggaaggc ttccgaaggt gcagagtatg acgatcagac ctctcagcgc  420
gaaaagagg acgataaggt gtttcccggc ggaagccata catacgtctg gcaggtgctg  480
aaggagaatg cccccatggc cagcgaccct gctgcctgac ctactcata tctgtcccac  540
gtggacctgg tgaaggatct gaacagcggg ctgatcggtg cactgctggt gtgtagagaa  600
ggctctctgg ccaaggagaa aactcagacc ctgcataagt tcattctgct gttcgccgtg  660
tttgacgaag gaaaaagctg gcactctgag actaagaact ccctgatgca ggacagggat  720
gcagcaagcg cacgagcttg gcccaaaatg cataccgtca acggctacgt gaatcgaagt  780
ctgcctggcc tgatcggatg ccaccgtaag tccgtctatt ggcatgtgat cgggatgggc  840
accacacccg aagtccacag cattttcctg gagggtcata cctttctggt gagaaaccac  900
cgccaggcat ccctggagat cagcccttatt actttcctga ccgcccagac actgctgatg  960
gatctgggcc agttcctgct gttttgccac atctccagcc accagcatga tggaatggag  1020
gcatacgtca aagtggactc ttgtcctgag gaaccacaac tgaggatgaa gaacaatgag  1080
```

```
gaagccgaag actatgacga tgacctgaca gactccgaga tggatgtggt ccgcttcgat     1140
gacgataact cccctagctt tatccagatt cgaagcgtcg ccaagaaaca cccaaagact     1200
tgggtgcatt acatcgcagc cgaggaagag gactgggatt atgctccact ggtgctggca     1260
cccgatgatc ggagttacaa atcacagtat ctgaacaatg ggcctcagcg aattggtcgt     1320
aagtacaaga aagtgcgatt catggcctat actgatgaaa cctttaagac acgtgaagct     1380
atccagcacg agtctgggat tctgggtcca ctgctgtacg gcgaagtggg agacacactg     1440
ctgatcattt ttaagaacca ggcaagcaga ccttacaata tctatccaca tggaattact     1500
gatgtccggc tctgtactc taggcggctg ccaaaggggg tgaaacacct gaaggacttc     1560
cccatcctgc ctggtgaaat ttttaagtac aagtggacag tcactgtgga ggatgggcca     1620
acaaagtctg accctcgatg cctgactcgt tactattcta gtttcgtgaa tatgaaaga     1680 gacctggcct ccgggctgat cggtcctctg ctgatttgtt acaaagagtc tgtggatcag     1740 agggcaacc agatcatgag tgacaagcgg aatgtcattc tgttcagcgt gtttgacgaa     1800
aacaggtctt ggtatctgac cgagaacatc cagcggttcc tgccaaatcc cgcaggcgtg     1860
cagcttgaag atccagagtt tcaggccagc aacatcatgc attctattaa tggatacgtg     1920
ttcgactctc tgcagttgag tgtctgtctg cacgaggtgg cctactggta tatcctgtct     1980
attggcgctc agactgattt cctgtcagtg ttcttttccg gatacacctt taagcataaa     2040
atggtgtatg aggacaccct gacactgttc cctttagtg gcgaaaccgt gtttatgtca     2100
atggagaatc ctggcctgtg gattctggga tgccacaact ccgatttcag aaatcgcggg     2160
atgaccgctc tgctgaaagt gtcatcctgt gacaagaaca ctggtgacta ctatgaagat     2220
agttacgagg acatctcagc ttatctgctg tccaaaaaca atgcaattga ccacgatct     2280 tttagtcaga atcctccagt gctgaagagg caccagcggg agatcacaag gactaccctg     2340
cagagtgatc aggaagagat cgactacgac gatactattt ccgtggaaat gaagaaagag     2400
gacttcgaca tctatgacga agatgagaac cagtcccca ggagcttcca agagaaaacc     2460
cgtcattact ttattgctgc agtggagcgc ctgtgggatt atggcatgag ctctagtcca     2520
cacgtcctgc gaaatcgtgc ccagtcaggc tccgtgcccc agttcaagaa agtggtcttc     2580
caggagttta cagacggctc ctttactcag ccactgtaca gaggagaact gaacgagcat     2640
ctgggcctgc tgggacccta tatccgcgcc gaagtcgagg ataacattat ggtgaccttc     2700
agaaatcagg ccagccgccc ctactctttt tattcatccc tgatcagcta cgaagaggac     2760
cagagacagg gcgctgaacc ccgcaaaaac ttcgtgaagc ctaatgagac taaaacctac     2820
ttttggaagg tgcagcacca catggcacct acaaagacg agttcgattg caaggcatgg     2880 gcctatttt cagacgtcga tctggagaag gacgtgcatt ctgggctgat cggtcccctg     2940
ctggtgtgtc atacaaacac tctgaatcct gctcacggca ggcaggtcac cgtgcaggaa     3000
tttgcactgt tctttaccat cttttgatgag acaaagtctt ggtactttac agaaaacatg     3060
gagagaaatt gccgcgctcc ttgtaatatt cagatggaag acccaacttt caaggagaac     3120
tatcggtttc atgcaatcaa tggctatatt atggatacc tgcctggact ggtcatggcc     3180
caggaccaga ggattcggtg gtatctgctg tctatgggga gtaacgagaa tatccacagt     3240
attcatttct caggtcacgt ctttaccgtg aggaagaaag aagagtataa aatggccctg     3300
tacaacctgt atccaggcgt cttcgaaaca gtggagatgc tgccctccaa ggctggaatc     3360
tggcgggtgg aatgcctgat tggggagcac ctgcatgcag gcatgtccac actgtttctg     3420
```

```
gtgtacagca ataagtgtca gactccactg gggatggcca gcggtcatat ccgggatttc   3480
cagattaccg cttctggcca gtacggacag tgggctccca agctggctag actgcactat   3540
agcggctcta tcaacgcctg gtccactaaa gagcccttct cctggattaa ggtggacctg   3600
ctggctccca tgatcattca tgggatcaaa acccagggtg cacgccagaa gttcagctct   3660
ctgtacatct ctcagtttat catcatgtac agtctggatg aaagaaatg  gcagacctac   3720
cgaggcaatt ccaccggaac actgatggtc ttctttggca acgtggacag ttcaggaatc   3780
aagcacaaca ttttcaatcc ccctatcatt gctcgataca tccgtctgca ccctacccat   3840
tattcaatta ggtccacact gcggatgaa  ctgatgggt gcgatctgaa cagttgttca    3900
atgccactgg gtatggagtc caaggcaatc agcgacgccc agattaccgc ttccagctac   3960
ttcactaata tgtttgccac ctggtccccc agcaaagcta ggctgcatct gcagggccga   4020
agcaacgcct ggcgtccaca ggtcaacaat cccaaggagt ggctgcaggt ggattttcag   4080
aaaacaatga aggtcactgg cgtgacaact cagggagtca atctctgct  gacaagtatg   4140
tacgtgaagg agttcctgat ctctagttca caggacggac accagtggac tctgttcttt   4200
cagaacggga aggtcaaagt gttccagggt aatcaggatt ccttcacccc tgtggtcaac   4260
tctctagacc cacccctgct gaccaggtat ctgcgaatcc acccacagag ctgggtccat   4320
cagattgctc tgagaatgga agtgctgggg tgcgaggcac aggatctgta tggatccggt   4380
ggcggtggct ccggtggagg cggaagcggc ggtgaggat caggcggtgg aggtagcggc    4440
ggaggcggta gctccagctc tagtaaagct cccctcctt ccctgccctc accctcaaga   4500
ctgcctggac cttccgacac tcccatcctg ccacaggtgg agtgccctcc atgtccagca   4560
cccctgtcg  caggtccatc tgtgttcctg tttccaccca agcctaaga  ccagctgatg   4620
atctcccgca ccccagaagt cacctgtgtg gtcgtggatg tgagccatga agaccccgag   4680
gtccagttca attggtacgt ggatggcgtc gaggtgcaca acgctaagac aaaacctaga   4740
gaagagcagt tcaactctac ctttcgcgtc gtgagtgtgc tgacagtcgt gcaccaggac   4800
tggctgaatg gcaaggagta aagtgcaaa  gtgagcaaca aggactgcc  tgcctcaatc   4860
gaaaagacta tttccaagac caaggacag  ccaagagagc cccaggtgta caccctgcct   4920
ccaagccgcg aagagatgac taaaaatcag gtctctctga cctgtctggt aagggggttt   4980
tatcctagtg atatcgccgt ggaatgggag tcaaacggtc agccagagaa caattacaag   5040
accacacccc ctatgctgga cagcgatggg tctttctttc tgtatagcaa actgacagtg   5100
gacaagtctc ggtggcagca gggtaacgtc ttctcttgca gtgtgctgca cgaagcactg   5160
cacaatcatt acacccagaa gtcactgtca ctgagcccag gaaaatga                 5208
```

<210> SEQ ID NO 18
<211> LENGTH: 5
<212> TYPE: PRT
<213> ORGANISM: Artificial sequence
<220> FEATURE:
<223> OTHER INFORMATION: flexible peptide linker

<400> SEQUENCE: 18

Gly Gly Gly Gly Ser
1               5

<210> SEQ ID NO 19
<211> LENGTH: 14
<212> TYPE: PRT
<213> ORGANISM: Artificial sequence
<220> FEATURE:

```
<223> OTHER INFORMATION: peptide linker repetitive unit

<400> SEQUENCE: 19

Gly Ser Gly Gly Ser Gly Gly Gly Ser Gly Gly Gly Gly Ser
1               5                   10

<210> SEQ ID NO 20
<211> LENGTH: 16
<212> TYPE: PRT
<213> ORGANISM: Homo sapiens

<400> SEQUENCE: 20

Ser Ser Ser Ser Lys Ala Pro Pro Pro Ser Leu Pro Ser Pro Ser Arg
1               5                   10                  15

<210> SEQ ID NO 21
<211> LENGTH: 20
<212> TYPE: PRT
<213> ORGANISM: Artificial sequence
<220> FEATURE:
<223> OTHER INFORMATION: CTP unit

<400> SEQUENCE: 21

Ser Ser Ser Ser Lys Ala Pro Pro Pro Ser Ser Ser Ser Ser Lys Ala
1               5                   10                  15

Pro Pro Pro Ser
            20
```

HIGHLY GLYCOSYLATED HUMAN BLOOD-CLOTTING FACTOR VIII FUSION PROTEIN, AND MANUFACTURING METHOD AND APPLICATION OF SAME

FIELD OF THE INVENTION

The present invention relates to the field of fusion proteins and, more specifically, to a fusion protein of human coagulation factor VIII (FVIII), its preparation method and uses, especially those uses in the treatment of various coagulation-related diseases.

BACKGROUND

Coagulation factor VIII (FVIII), also known as antihemophilic factor, plays a critical role in the endogenous coagulation system. Based on a large number of studies of FVIII molecular genetics, the deficiency of FVIII in sex chromosome X-linked genes will lead to type A hemophilia. According to statistics, hemophilia A has a prevalence rate of 1/5000 in the male population, accounting for more than 80% of the total number of hemophilia patients. The current common treatment for hemophilia A is the replacement therapy, that is, to supplement coagulation factor VIII that hemophilia patients lack.

FVIII is a multi-domain macromolecular glycoprotein, which is divided into six domains: three A domains (A1, A2, A3), one carbohydrate-rich and non-essential central B domain (B), and two C domains (C1, C2). The mature protein consists of a light chain and a heavy chain and has a molecular weight of approximately 280 kDa. The light chain has a molecular weight of about 80 kDa and comprises A3, C1 and C2 domains, with a linking mode of A3-C1-C2. The heavy chain has a molecular weight of about 90 to 200 kDa and comprises A1, A2 and B domains, with a linking mode of A1-A2-B. The association between the heavy chain and light chain is metal ion-dependent. In plasma, the dimer formed by the heavy chain and light chain is protected from premature degradation by binding to von Willebrand factor (vWF) with high affinity. The half-life of non-activated FVIII, bound to vWF in plasma, is about 12 h. FVIII is activated by activated factor FX (FXa) and thrombin through proteolytic cleavage at amino acids Arg 372 and Arg 740 in the heavy chain and at Arg 1689 in the light chain, resulting in the release of vWF factor and the generation of activated FVIII dimer (FVIIIa). In the presence of Ca2+, FVIIIa forms a close complex with activated coagulation factor FIX (FIXa) and FX on the phospholipid surface. FX is then activated by FIXa and the activated FX (FXa) is dissociated from the complex. FXa converts prothrombin to thrombin, which converts fibrinogen directly to fibrin. As a cofactor of the coagulation system, FVIII is able to enhance the efficiency of FIXa to activate FX by several orders of magnitude.

The FVIII molecule is one of the longest gene fragments cloned to date and is the protein drug with the largest molecular weight used in clinical practice. For recombinant proteins with high molecular weight and high degree glycosylation, mammalian cells are the optimal expression system. However, the in vitro expression yield of recombinant FVIII is significantly lower than those of other genes of similar nature. For example, the expression level of FVIII is only 1% of FIX. The low level expression of FVIII may be a reflection of the body's demand for FVIII, but it is undoubtedly a major obstacle to the in vitro expression of recombinant FVIII. In addition, because the half-life of FVIII in the blood is short, only 8-12 h, severe hemophilia A patients with prophylactic treatment must receive intravenous (i.v.) injection about 3 times a week.

For prolonging the in vivo functional half-life of FVIII, current techniques are to link FVIII to half-life prolonging moieties such as PEG, human serum albumin (HSA), transferrin, or IgG Fc. For example, pharma companies Novo Nordisk, Bayer, and Baxter have developed long-acting PEGylated FVIII products N8-GP, BAY94-9027, and BAX 855, respectively, which have entered clinical studies. However, the additional step of chemical conjugation of PEG to FVIII in the protein preparation process has reduced the final yield and increased the cost of preparation. Pharmacokinetic data show that PEGylated FVIII does not achieve a significantly longer half-life. For example, N8-GP had a circulation half-life of about 18 h in patients with hemophilia A (Tiede A et al., J Thromb Haemost, 2013, 11:670-678). A clinical phase I study of BAY94-9027 showed that its half-life in healthy humans was about 18.2 h, about 1.4 times longer than that of wild-type FVIII (Coyle T et al., Haemophilia, 2012, 18 (Suppl 3):22). The half-life of Bax 855 was about 18 h (Turecek PL et al., Hamostaseologie, 2012, 32 Suppl 1:S29-38).

The monomer-dimer hybrid rFVIIIFc fusion protein Eloctate®, developed by Biogen Idec, USA, was approved by the US Food and Drug Administration in June 2014. Clinical data showed that Eloctate® extended the half-life in humans by 1.5 to 1.7 fold (Dumont J A et al., Blood, 2012, 119: 3024-3030; Powell JS et al., Blood, 2012, 119:3031-3037), which needed to be injected once every 3 to 5 days. It was reported that Biogen constructed a double expression vector containing the genes of both rFVIIIFc and Fc. After the vector was transfected into HEK-293 cells, the fusion of rFVIIIFc in homodimer form was not detected in the expressed products as expected, and only the monomer-dimer hybrid rFVIIIFc fusion protein and the Fc dimer were detected. The researchers from the company speculated as follows. As the molecular size of the homodimer form was too large for the expression system, the host cells failed to secrete the rFVIIIFc homodimer protein with a molecular weight of about 400 kDa, or the rFVIIIFc monomer did not aggregate due to the steric hindrance effect (Peters R T et al., J Thromb Haemost, 2013, 11(1):132-141). Therefore, the expression of the homodimer form of the FVIII fusion protein was quite difficult.

The carboxyl terminal peptide (hereinafter referred to as CTP) of the human chorionic gonadotropin (hCG) beta chain has the effect of prolonging the in vivo half-life of certain proteins. Thus the half-life prolonging moieties can be selected from the immunoglobulin Fc fragment, HSA, CTP, or others as in the fusion proteins disclosed in some patent documents. In addition, CTP can also be used as a linker, mainly used to link different subunits of the same protein. For example, CTP is used as a linker to link the beta and alpha subunits of follicle stimulating hormone, as disclosed in Chinese Patent Nos. CN103539860A, CN103539861A, CN103539868A, and CN103539869A. As another example, CTP is used as a linker to link the beta and alpha subunits of glycoprotein hormone as disclosed in the patent WO2005058953A2.

The present inventors do not use CTP as a linker or as a half-life prolonging moiety as suggested by the prior art, but instead connect it to a flexible peptide linker (e.g., (GGGGS)n (SEQ ID NO: 18)) to constitute a new linker sequence. The new linker is located between FVIII and the half-life prolonging moiety (e.g., the immunoglobulin Fc fragment, which does not contain the CTP as suggested by the prior art) to constitute a new FVIII fusion protein, further prolonging the half-life and maintaining the biological activity and function of FVIII.

DESCRIPTION OF THE INVENTION

The present invention provides a highly glycosylated Fc fusion protein of coagulation factor VIII in homodimer form. The fusion protein has a prolonged in vivo active half-life and similar biological activity to recombinant FVIII. In addition, the present invention provides a method for the efficient and stable expression of the fusion protein. The fusion protein expressed by the method has advantages of high yield, good stability in the preparation and storage processes, and similar biological activity to recombinant FVIII factors on the market.

The first aspect of the present invention provides a highly glycosylated FVIII fusion protein (hereinafter abbreviated as fusion protein) comprising, sequentially from the N- to C-terminus, human coagulation factor VIII (hFVIII), a flexible peptide linker (L), at least one rigid carboxyl terminal peptide unit of the human chorionic gonadotropin beta subunit (hereinafter abbreviated as rigid CTP unit, expressed as (CTP)n, preferably n is 1, 2, 3, 4, or 5), and a half-life prolonging moiety (e.g., a immunoglobulin Fc fragment, albumin, transferrin or PEG, preferably a human IgG Fc variant (expressed as vFc)). In some preferred embodiments of the present invention, the fusion protein is expressed as hFVIII-L-CTPn-vFc.

Wherein, the hFVIII is a wild type or a mutant thereof; further, the wild type hFVIII has the amino acid sequence as shown in SEQ ID NO: 1; preferably, the hFVIII mutant has at least 85% identity to the amino acid sequence shown in SEQ ID NO: 1; more preferably, the hFVIII mutant has at least 90% identity to the amino acid sequence shown in SEQ ID NO: 1; and most preferably, the hFVIII mutant has at least 95% identity to the amino acid sequence shown in SEQ ID NO: 1.

Wherein, preferably, the flexible peptide linker is non-immunogenic and can generate a sufficient spatial distance between hFVIII and Fc to minimize the steric hindrance between them. Preferably, the flexible peptide linker consists of two or more amino acid residues selected from the following several amino acids: Gly (G), Ser (S), Ala (A) and Thr (T).

More preferably, the flexible peptide linker comprises G and S residues. The length of the peptide linker is important for the activity of the fusion protein. In the present invention, the peptide linker may preferably comprise a general amino acid sequence formula formed by combining repetitive unit(s), $(GS)_a(GGS)_b(GGGS)_c(GGGGS)_d$ (SEQ ID NO: 19), wherein a, b, c and d are integers greater than or equal to 0, and a+b+c+d≥1.

Specifically, in the embodiments of the present invention, the peptide linker may preferably comprise the following sequences:

```
(i) L1: GSGGGSGGGGSGGGGS
    (as shown in SEQ ID NO: 2);

(ii) L2: GSGGGGSGGGGSGGGGSGGGGSGGGGS
    (as shown in SEQ ID NO: 3);

(iii) L3: GGGGSGGGGSGGGGSGGGGS
    (as shown in SEQ ID NO: 4);

(iv) L4: GSGGGGSGGGGSGGGGSGGGGSGGGGSGGGGSGGGGS
    (a shown in SEQ ID NO: 5);

(v) L5: GGGSGGGSGGGSGGGSGGGS
    (as shown in SEQ ID NO: 6);
```

Wherein, the rigid CTP unit is selected from the full length sequence consisting of carboxyl terminal amino acids 113 to 145 of the human chorionic gonadotropin β subunit or a fragment thereof. Specifically, the rigid CTP unit comprises the amino acid sequence as shown in SEQ ID NO: 7 or a truncated sequence thereof. First, the CTP peptide that occurs naturally in the human body and contains multiple glycosylation sites is non-immunogenic. Second, compared to the random coil of the flexible peptide linker, the rigid CTP peptide linker containing multiple glycosylation sites can form a stable steric conformation, which allows the FVIII and Fc segments to fold independently into correct three-dimensional conformations without affecting biological activities of each other. Moreover, the glycosyl side chains of CTP has a protective effect which can reduce the sensitivity of the peptide linker to proteases.

Preferably, the rigid CTP unit contains at least 2 glycosylation sites. For example, in a preferred embodiment of the present invention, the rigid CTP unit contains 2 glycosylation sites. Illustratively, the rigid CTP unit contains 10 N-terminal amino acids of SEQ ID NO: 7, i.e. SSSS*KAPPPS* (SEQ ID NO: 9), or the rigid CTP unit contains 14 C-terminal amino acids of SEQ ID NO: 7, i.e. S*RLPGPS*DTPILPQ (SEQ ID NO: 10). As another example, in another embodiment, the rigid CTP unit contains 3 glycosylation sites. Illustratively, the rigid CTP unit contains 16 N-terminal amino acids of SEQ ID NO: 7, i.e. SSSS*KAPPPS*LPSPS*R (SEQ ID NO: 20). As yet another example, in other embodiments, the rigid CTP unit contains 4 glycosylation sites. Illustratively, the rigid CTP unit contains 28, 29, 30, 31, 32, or 33 amino acids, starting from position 113, 114, 115, 116, 117, or 118 and ending at position 145 of the human chorionic gonadotropin beta subunit. Specifically, the rigid CTP unit contains N-terminal amino acids of SEQ ID NO: 7, i.e. SSSS*KAPPPS*LPSPS*RLPGPS*DTPILPQ (SEQ ID NO: 8). In this context, * represents a glycosylation site. Each possibility represents a separate embodiment of the present invention.

In other embodiments, the rigid CTP units provided by the present invention have at least 70% identity to the native CTP amino acid sequence. In other embodiments, the rigid CTP units provided by the present invention have at least 80% identity to the native CTP amino acid sequence. In other embodiments, the rigid CTP units provided by the present invention have at least 90% identity to the native CTP amino acid sequence. In other embodiments, the rigid CTP units provided by the present invention have at least 95% identity to the native CTP amino acid sequence.

Preferably, the rigid CTP units described in the specific embodiments of the present invention may comprise the following sequences:

```
(i) CTP1: PRFQDSSSSKAPPPSLPSPSRLPGPSDTPILPQ
    (as shown in SEQ ID NO: 7);

(ii) CTP2: SSSSKAPPPSLPSPSRLPGPSDTPILPQ
    (as shown in SEQ ID NO: 8);

(iii) CTP3: SSSSKAPPPS
    (as shown in SEQ ID NO: 9);
```

-continued (iv) CTP4: SRLPGPSDTPILPQ
    (as shown in SEQ ID NO: 10).

In some embodiments of the present invention, the fusion protein comprises one of the rigid CTP units described above.

In other embodiments of the present invention, the fusion protein contains more than one of the rigid CTP units described above, preferably contains 2, 3, 4 or 5 rigid CTP units described above. For example, in one embodiment of the present invention, the fusion protein contains two rigid $CTP^3$ units: SSSSKAPPPSSSSSKAPPPS (SEQ ID NO: 21) ($CTP^3$-$CTP^3$, or expressed as $(CTP^3)_2$).

Wherein, preferably, the half-life prolonging moiety is selected from an Fc fragment of immunoglobulin IgG, IgM, or IgA, and more preferably from an Fc fragment of human $IgG_1$, $IgG_2$, $IgG_3$ or $IgG_4$ and variants thereof. Further, the human IgG Fc variants contain at least one amino acid modification relative to the wild type human IgG Fc, and have reduced effector functions (antibody-dependent cell-mediated cytotoxicity (ADCC) and/or complement-dependent cytotoxicity (CDC) effects) and/or an enhanced binding affinity for the neonatal receptor FcRn. Further, the human IgG Fc variants may be selected from the following group:

(i) $vFc\gamma_1$: human $IgG_1$ hinge, $C_H2$ and $C_H3$ regions containing Leu234Val, Leu235Ala and Pro331Ser mutations, and having the amino acid sequence as shown in SEQ ID NO: 11;

(ii) $vFc\gamma_{2-1}$: human $IgG_2$ hinge, $C_H2$ and $C_H3$ regions containing Pro331Ser mutation, and having the amino acid sequence as shown in SEQ ID NO: 12;

(iii) $vFc\gamma_{2-2}$: human $IgG_2$ hinge, $C_H2$ and $C_H3$ regions containing Thr250Gln and Met428Leu mutations, and having the amino acid sequence as shown in SEQ ID NO: 13;

(iv) $vFc\gamma_{2-3}$: human $IgG_2$ hinge, $C_H2$ and $C_H3$ regions containing Pro331Ser, Thr250Gln and Met428Leu mutations, and having the amino acid sequence as shown in SEQ ID NO: 14;

(v) $vFc\gamma_4$: human $IgG_4$ hinge, $C_H2$ and $C_H3$ regions containing Ser228Pro and Leu235Ala mutations, and having the amino acid sequence as shown in SEQ ID NO: 15.

The IgG Fc variants provided by the present invention include, but are not limited to, the five variants described in (i) to (v), and may also be those obtained by combining or adding the mutation sites of two functional variants of the same IgG subtype. For example, the variant described in (iv) above is a new IgG2 Fc combination variant obtained by adding the mutation sites in (ii) and (iii).

The Fc variants (vFcs) in the fusion proteins of the present invention contain the hinge, CH2 and CH3 regions of human IgG, e.g., human IgG1, IgG2 and IgG4. The CH2 region contains amino acid mutations at positions 228, 234, 235 and 331, defined by the EU numbering system, and it is believed that these amino acid mutations can reduce the effector functions mediated by the Fc region. Human IgG2 does not bind to FcγRs and exhibits very weak complement activity. The Fcγ2 variants with Pro331Ser mutation have lower complement activity than native Fcγ2 and are still non-binders to FcγRs. IgG4 Fc is deficient in activating the complement cascade and its binding affinity for FcγRs is about an order of magnitude lower than that of IgGI Fc. The Fcγ4 variants with Leu235Ala mutation exhibit minimum effector functions as compared to native Fcγ4. The Fcγ1 variants with Leu234Val, Leu235Ala and Pro331Ser mutations also exhibit reduced effector functions as compared to native Fcγ1. The above Fc variants are more suitable for the preparation of FVIII fusion proteins than native human IgG Fcs. The amino acid mutations at 250 and 428 positions, defined by the EU numbering system, increase the binding affinity of the Fc region for the neonatal receptor FcRn, thereby further prolonging the half-life (Paul R et al., J Biol Chem, 2004, 279:6213-6216). The above two types of functional variants are combined or added on each other to generate new combination variants to reduce the effector functions while prolonging the half-life. The Fc variants of the present invention contain mutations that are not limited to the above-described sites, but may also introduce substitutions at other sites such that Fcs have reduced effector functions and/or enhanced binding to FcRn. Meantime, these mutations do not lead to reduction of the function/activity of the Fc variants or undesirable conformational changes. Common mutation sites may be found in Shields R L et al., J Biol Chem, 2001,276(9):6591-604.

In a preferred embodiment of the present invention, the amino acid sequence of the fusion protein is shown in SEQ ID NO: 16.

The second aspect of the present invention provides a DNA molecule encoding any one of the above-described fusion proteins.

In a preferred embodiment of the present invention, the DNA sequence of the fusion protein is shown in SEQ ID NO: 17.

Yet another aspect of the present invention provides a vector containing the DNA molecule described above.

Yet another aspect of the present invention provides a host cell containing or transfected with the above-described vector.

In a particular embodiment of the invention, the host cell is a CHO-derived cell strain DG44.

The fifth aspect of the present invention provides a pharmaceutical composition. The pharmaceutical composition comprises a pharmaceutically acceptable carrier, excipient and/or diluent, and an effective amount of the above-described fusion protein.

Another aspect of the present invention provides a method for preparing or producing the fusion protein from a mammalian cell line, e.g., a CHO-derived cell line, which comprises the steps of:

(a) introducing the DNA molecule encoding the fusion protein into a mammalian cell line to produce a CHO-derived cell line;

(b) screening the cell strains of step (a) to obtain a high-yield cell strain expressing more than 1 IU/106 cells per 24 h in its growth medium;

(c) culturing the cell strain obtained in step (b) to express the fusion protein;

(d) harvesting the fermentation broth of step (c) and isolating and purifying the fusion protein.

Further, the CHO-derived cell line in step (a) is DG44.

Further, the cell cultivation in step (c) may be carried out by using a batch, perfusion or fed-batch culture method.

Further, in step (d), the fusion protein is purified by a four-step chromatography procedure, i.e., affinity chromatography, hydrophobic chromatography, anion exchange chromatography, and molecular sieve chromatography. The present invention further gives the preferred purification conditions in Example 5.

In a preferred embodiment of the present invention, the fusion protein prepared by the above method has an activity of >6000 IU/mg.

The sixth aspect of the present invention provides use of the fusion protein in the manufacture of a drug for the prevention or treatment of a hemorrhagic disease or event resulting from a deficiency or functional defect of FVIII.

Further, the disease includes type A hemophilia. The fusion proteins of the present invention play a role in controlling or preventing the occurrence of bleeding in spontaneous bleeding events, surgical prophylaxis, perioperative period management, or surgical treatment in hemophilia A patients.

The present inventors have found that the advantages of both the fusion proteins and their preparation methods described and/or disclosed in the present invention can be summarized as follows:

1. The FVIII fusion protein constructed by the present invention is non-lytic, that is, by mutating the complement and receptor binding region of the Fc segment and adjusting the binding affinity of Fc for the corresponding receptor, the ADCC and CDC effects are reduced or eliminated, while only the role of the Fc segment for prolonging the in vivo half-life of the active protein is kept without the generation of cytotoxicity. The Fc segment of the FVIII fusion protein developed by Biogen is from a natural source. It is predictable that the Fc-mediated adverse effector functions will increase treatment risks to patients.

2. The present invention adopts CHO cells for expressing the fusion proteins. Only the homodimeric FVIII Fc fusion protein exists in the expression products, and the purification step is simple and efficient. For expressing the monomer-dimer hybrid (Monomeric) FVIII fusion protein, Biogen constructed a double expression vector that expressed both rFVIIIFc and Fc, which was to be transfected into HEK-293 cells (U.S. Publication No. US20130274194A1). Three forms of protein expression products were expected to be in the fermentation broth, the FVIII-Fc:FVIII-Fc homodimeric (Dimeric) fusion protein, the FVIII-Fc:Fc monomer-dimer hybrid (Monomeric) fusion protein, and the Fc:Fc dimer. During the fusion protein expression process, the host cells needed to express both FVIII-Fc and Fc single chain molecules simultaneously, and then the molecules bound to each other to form the above three products, such that the final expression efficiency of the target product was greatly reduced. In addition, in the purification process, the other two forms of side products had also to be removed. Hence, the purification process was more complex and the production efficiency was lower, such that the production cost was greatly increased. Compared to that of the Monomeric rFVIIIFc fusion protein developed by Biogen, the preparation method of the present invention has certain technical and price advantages. The expression and purification process of the present invention is simpler and more efficient and the production cost is lower.

3. HemA mice were given the FVIII fusion protein FP-B of the present invention at doses of 30 IU/kg, 90 IU/kg and 270 IU/kg, respectively. In the middle and high dose groups, acute hemorrhage in the HemA mice could be effectively controlled, and the mouse survival rate of groups given each dose of FP-B were higher than the group given recombinant FVIII, Xyntha (Pfizer), indicating that the fusion protein FP-B had a more lasting pharmacodynamic effect than Xyntha. Meantime, both of bleeding time and volume results in the high and low FP-B dose groups showed dose-dependent relations.

4. Compared to the recombinant FVIII, Xyntha, the fusion protein of the present invention may be expected to have reduced immunogenicity and reduced production of neutralizing antibodies in patients.

5. The fusion proteins provided by the present invention have high biological activities. The activity of each batch of purified fusion proteins is in the range of 6000-10000 IU/mg. When expressed in molar specific activity, it is about 2340-3900 IU/nM fusion protein, corresponding to 1170-1950 IU/nM FVIII, as each fusion protein molecule contains two FVIII molecules. In some batches, the activity of the purified fusion protein is even more than 12000 IU/mg, expressed in molar specific activity as about 4680 IU/nM fusion protein, corresponding to 2340 IU/nM FVIII. Thus, the activity of the fusion protein provided by the present invention is comparable to or even higher than that of the monomer-dimer hybrid rFVIIIFc fusion protein (1660-1770 IU/nM), developed by Biogen (J. McCue et al., Biologicals, 2015,43:213-219), and that of recombinant FVIII ReFacto (1521-2287 IU/nM) on the market (U.S. Publication No. US20130274194A1). This indicates that the Fc segment fused to the C-terminus of the fusion protein of the present invention has little effect on the activity of FVIII.

6. The fusion protein provided by the present invention contains a rigid CTP polypeptide with multiple glycosyl side chains, which can form a stable steric conformation compared to the random coil of a flexible linker such as (GGGGS)n (SEQ ID NO: 18). This "separation" effect causes the FVIII and Fc segments to fold independently into correct three-dimensional conformations without affecting biological activities of each other. CTP possesses glycosyl groups. Highly sialylated, negatively charged CTP can resist the clearance by the kidney, further prolonging the half-life of the fusion protein. Moreover, the protective effect of side chains of CTP can reduce the sensitivity of the peptide linker to proteases, such that the fusion protein is not easily degraded in the linking region.

7. The fusion protein of the invention has good stability in the processes of fermentation, purification and storage.

8. The preparation method of the fusion protein provided by the invention has the advantage of high yield. After cells are cultured in a 300 mL shake flask for 14 days, the cumulative yield can reach at least 150 mg/L, which can be scaled up to realize large-scale industrial production.

It should be understood that within the scope of the present invention, the above-described technical characteristics of the present invention and those described specifically in the followings (e.g., examples) may be combined with each other to produce a new or preferred technical solution.

DETAILED DESCRIPTION OF THE INVENTION hCG-β Carboxyl Terminal Peptide (CTP)

CTP is a short peptide from the carboxyl terminus of the human chorionic gonadotropin (hCG) beta subunit. Four kinds of reproduction-related polypeptide hormones, follicle stimulating hormone (FSH), luteinizing hormone (LH), thyroid stimulating hormone (TSH), and human chorionic gonadotropin (hCG) contain the same alpha subunit and their respective specific beta subunits. Compared with the other three hormones, hCG has a significantly prolonged in vivo half-life, which is mainly due to the specific carboxyl terminal peptide (CTP) on the hCG β-subunit (Fares F A et al., Proc Natl Acad Sci USA, 1992, 89 (10):4304-4308). The natural CTP contains 37 amino acid residues and has four O-glycosylation sites. At the terminus are sialic acid residues. Highly sialylated, negatively charged CTP can resist the clearance by the kidney, thereby prolonging the in vivo half-life of the protein (Fares F A et al., Proc Natl Acad Sci USA, 1992, 89(10):4304-4308). The present inventors creatively connect at least one CTP peptide with a flexible peptide linker of an appropriate length to constitute a new peptide linker, which links FVIII to a half-life prolonging moiety, e.g., an immunoglobulin Fc fragment.

The present inventors have found that the addition of a CTP peptide between FVIII and an Fc variant is equivalent to the addition of a rigid peptide linker. On one hand, the addition of the CTP peptide ensures that the N-terminally fused FVIII does not affect the binding site of Fc variant for FcRn, thus having no effect on the half-life. In addition, the protein A binding site of Fc is important for the purification step. The addition of the CTP peptide ensures that the N-terminally fused FVIII will not "block" its binding site for protein A, allowing for choosing a cheaper and more suitable beads to purify the fusion protein and reducing purification costs. On the other hand, the addition of the CTP peptide prevents the about 25 kD-sized Fc segment from interfering with the correct folding of the N-terminally fused FVIII, thus leading to no loss or decline of the biological activity/function of FVIII. The rigid CTP peptide containing multiple glycosyl side chains can form a stable steric conformation compared to the random coil of a flexible linker such as (GGGGS)n (SEQ ID NO: 18). This "separation" effect causes the FVIII and Fc segments to fold independently into correct three-dimensional conformations without affecting the biological activities of each other. Moreover, the protective effect of the glycosyl side chains of CTP reduces the sensitivity of the peptide linker to proteases, such that the fusion protein is not easy to be degraded in the linking region.

IgG Fc Variants

Non-Lytic Fc Variants

The Fc element is derived from the constant region Fc fragment of immunoglobulin IgG, and plays an important role in the eradication of pathogens in immune defense. The Fc-mediated effector functions of IgG are carried out through two mechanisms: (1) After binding to the Fc receptors (FcγRs) on the cell surface, the pathogen is broken down by phagocytosis or lysis or by the killer cell through the antibody-dependent cell-mediated cytotoxicity (ADCC) pathway. Alternatively, (2) after binding to C1q of the first complement component C1, the complement-dependent cytotoxicity (CDC) pathway is triggered and thus the pathogen is lysed. Among the four human IgG subtypes, IgG1 and IgG3 are able to bind to FcγRs effectively, and IgG4 has lower binding affinity for FcγRs. The binding of IgG2 to FcγRs is too low to be measured, so human IgG2 has little ADCC effects. In addition, human IgG1 and IgG3 can also effectively bind to C1q to activate the complement cascade. Human IgG2 binds weakly to C1q and IgG4 does not bind to C1q (Jefferis R et al., Immunol Rev, 1998, 163: 59-76), so the CDC effect of human IgG2 is also weak. Obviously, none of the native IgG subtypes is well suitable for constructing FVIII-Fc fusion proteins. For obtaining non-lytic Fc variants without the effector functions, the most effective method is to mutate the complement and receptor binding regions of the Fc segment and adjust the binding affinity of Fc for its related receptors to reduce or eliminate the ADCC and CDC effects. Eventually, the biological activity of the function protein and the long in vivo half-life of FVIII are retained without the generation of cytotoxicity. More mutation sites contained in non-lytic Fc variants can be found in Shields R L et al., J Biol Chem, 2001,276(9):6591-604 or China Patent No. CN 201280031137.2.

Fc Variants with Enhanced Affinity for the Neonatal Receptor FcRn

The plasma half-life of IgG depends on its binding to FcRn. Typically, IgG binds to FcRn at pH 6.0 and dissociates from FcRn at pH 7.4 (plasma pH). Through the study of the binding sites of the two, the sites on IgG that bind to FcRn are modified to increase the binding affinity at pH 6.0. It has been shown that mutations of some residues in the Fcγ domain, which are important for the binding of IgG to FcRn, can increase the plasma half-life of IgG. Mutations of residues T250, M252, S254, T256, V308, E380, M428 and N434 have been reported to increase or decrease the FcRn binding affinity (Roopenian et al., Nat. Review Immunology7:715-725,2007). Variants of Trastuzumab (Herceptin, Genentech), disclosed in Korean Patent No. KR 10-1027427, show increased FcRn binding affinity, and these variants contain one or more amino acid modifications selected from 257C, 257M, 257L, 257N, 257Y, 279Q, 279Y, 308F and 308Y. Variants of Bevacizumab (Avastin, Genentech), provided in Korean Patent No. KR 2010-0099179, show prolonged in vivo half-life by containing amino acid modifications at N434S, M252Y/M428L, M252Y/N434S and M428L/N434S. In addition, Hinton et al. also found that two variants T250Q and M428L increased the binding affinity for FcRn by 3 and 7 times, respectively. When the two sites were mutated simultaneously, the binding affinity was increased by 28 times. In rhesus macaque, the M428L or T250Q/M428L variant shows a 2-fold increase in plasma half-life (Paul R. Hinton et al., J Immunol, 2006, 176:346-356). More mutation sites contained in Fc variants with increased binding affinity for FcRn can be found in China Patent No. CN201280066663.2. In addition, studies show that the T250Q/M428L mutations in the Fc regions of five humanized antibodies improve the interaction between the Fc domain and FcRn. Moreover, in subsequent in vivo pharmacokinetic tests, compared to wild type antibodies, the Fc mutated antibodies show improved pharmacokinetic parameters, such as increased in vivo exposure, reduced clearance, and increased subcutaneous bioavailability, when administered via subcutaneous injection (Datta-Mannan A et al., MAbs. Taylor & Francis, 2012, 4(2):267-273.).

Fusion Proteins and Their Preparation Methods

The fusion protein gene of the present invention is artificially synthesized after codon optimization. Based on the nucleotide sequence of the present invention, a person skilled in the art is able to produce the coding nucleic acid molecule by various known methods conveniently. These methods are not limited to artificial synthesis and traditional subcloning, etc., and specific methods can be found in Molecular Cloning: A Laboratory Manual by J. Sambrook. In one embodiment of the present invention, the coding nucleic acid sequence of the present invention is constructed by synthesis of segments of nucleotide sequences followed by subcloning.

The present invention also provides an expression vector for a mammalian cell comprising a sequence encoding the fusion protein of the present invention and an expression regulatory sequence that is linked operably thereto. The term "linked operably" refers to a condition in which certain portions of a linear DNA sequence are capable of regulating or controlling the activity of other portions of the same linear DNA sequence. For example, if the promoter controls the transcription of a DNA sequence, then it is operably linked to the coding sequence.

The mammalian cell expression vectors may be commercially available, for example, including, but not limited to, pcDNA3, pIRES, pDR, pBK, pSPORT, etc. These vectors can be used for expression in a eukaryotic cell expression system. One skilled in the art can also select a suitable expression vector based on the host cell.

Based on the restriction map of a known empty expression vector, those skilled in the art can construct the recombinant expression vector of the present invention by the conventional method, that is, inserting the coding sequence of the fusion protein of the present invention into suitable restriction sites by restriction enzyme digestion and ligation.

The present invention also provides a host cell for expressing the fusion protein of the present invention comprising the coding sequence of the fusion protein of the present invention. The host cells are preferably eukaryotic cells, such as, but not limited to, CHO cells, COS cells, 293 cells, RSF cells, etc. In a preferred embodiment of the present invention, the cells are CHO cells which are better capable of expressing the fusion protein of the present invention, and producing a fusion protein with good activity and stability.

The present invention also provides a method for preparing the fusion protein of the present invention by recombinant DNA technology, which comprises the steps of:

(1) providing a nucleic acid sequence encoding the fusion protein;

(2) inserting the nucleic acid sequence of step (1) into a suitable expression vector to construct a recombinant expression vector;

(3) introducing the recombinant expression vector of step (2) into a suitable host cell;

(4) culturing the transfected host cells under conditions suitable for expression;

(5) collecting the supernatant and purifying the fusion protein produced.

The introduction of the coding sequence into a host cell can take a variety of known techniques in the art, such as, but not limited to, calcium phosphate precipitation, liposome-mediated transfection, electroporation, microinjection, viral infection method, and alkali metal ion method.

The cultivation of host cells and protein expression can be found in Olander R M et al., Dev Biol Stand 1996, 86:338. The cells and cell debris in the suspension can be removed by centrifugation to collect the supernatant.

The fusion protein prepared and obtained as described above can be purified as follows to a substantially homogeneous form, for example, showing a single or specific bands on an SDS-PAGE gel. First, the supernatant is concentrated and the concentrate can be further purified by gel filtration chromatography or ion exchange chromatography, such as anion or cation exchange chromatography. The gel matrix can be agar, glucan, polyamide and other media commonly used in protein purification. The Q- or SP-group is an ideal group for ion exchange. The purified product can be further purified by hydroxyapatite adsorption chromatography, metal chelate chromatography, hydrophobic interaction chromatography, and reverse phase high performance liquid chromatography, etc. All of the above purification steps can take different combinations to ultimately achieve a high protein purity and homogeneity. The expressed fusion protein can also be purified by using an affinity chromatography column containing antibody, receptor or ligand specific to the fusion protein. Depending on the properties of the affinity column used, the fusion protein bound to the affinity column can be eluted using conventional methods such as high salt buffer, pH change, etc.

Pharmaceutical Composition

The present invention also provides a pharmaceutical composition comprising an effective dose (preferably about 2 to 10 µg/kg) of a fusion protein of the invention and a pharmaceutically acceptable carrier. In general, an effective amount of the fusion protein of the present invention may be formulated in a non-toxic, inert and pharmaceutically acceptable aqueous carrier medium, wherein the pH is generally about 5-8, preferably about 6-8. The term "effective amount" or "effective dose" refers to an amount that yields functional or active effects on humans and/or animals and is acceptable by humans and/or animals. "Pharmaceutically acceptable" ingredients are those that are suitable for use in humans and/or mammals without excessive adverse side effects (e.g., toxicity, irritation and allergies), i.e., substances with a reasonable benefit/risk ratio. The term "pharmaceutically acceptable carrier" refers to a carrier for delivering a therapeutic agent, and the carrier includes various excipients and diluents.

Pharmaceutically acceptable carriers include, but are not limited to, saline, buffer, glucose, water, glycerol, ethanol, and combinations thereof. In general, the pharmaceutical formulation should be compatible with the mode of administration. The pharmaceutical compositions of the present invention may be prepared in the form of injections, for example, prepared by conventional methods using physiological saline or aqueous solutions containing glucose and other adjuvants. The pharmaceutical compositions described above are preferably manufactured under aseptic conditions. The amount of the active ingredient administered is the therapeutically effective amount. The pharmaceutical formulation of the present invention can also be prepared in a sustained release form.

The effective amount of the fusion protein of the present invention may vary depending on the mode of administration and the severity of the disease to be treated. A preferred effective amount may be determined by one of ordinary skill in the art based on various factors for example by clinical trials. The factors include, but are not limited to, the pharmacokinetic parameters of the fusion protein such as bioavailability, metabolism, half-life, etc., the severity of the disease to be treated in a patient, the patient's weight, the patient's immune status, the route of administration, etc.

BRIEF DESCRIPTION OF THE FIGURES

FIG. 1. The nucleotide sequence of FP-B in the SpeI-EcoRI (the restriction sites are underlined) fragment in the pcDNA3 expression vector and the derived amino acid sequence according to an example of the present invention. Human FVIII consists of a signal peptide (amino acids 1-19, underlined with " ... ") and a mature FVIII protein (amino acids 20-1457). The mature fusion protein comprises hFVIII (amino acids 20-1457), a flexible peptide linker (amino acids 1458-1484, underlined with "_____"), a rigid CTP unit (amino acids 1485-1512, underlined with "_____"), and a vFcγ2-3 variant (amino acids 1513-1735).

EXAMPLES

Example 1

Figure 2:
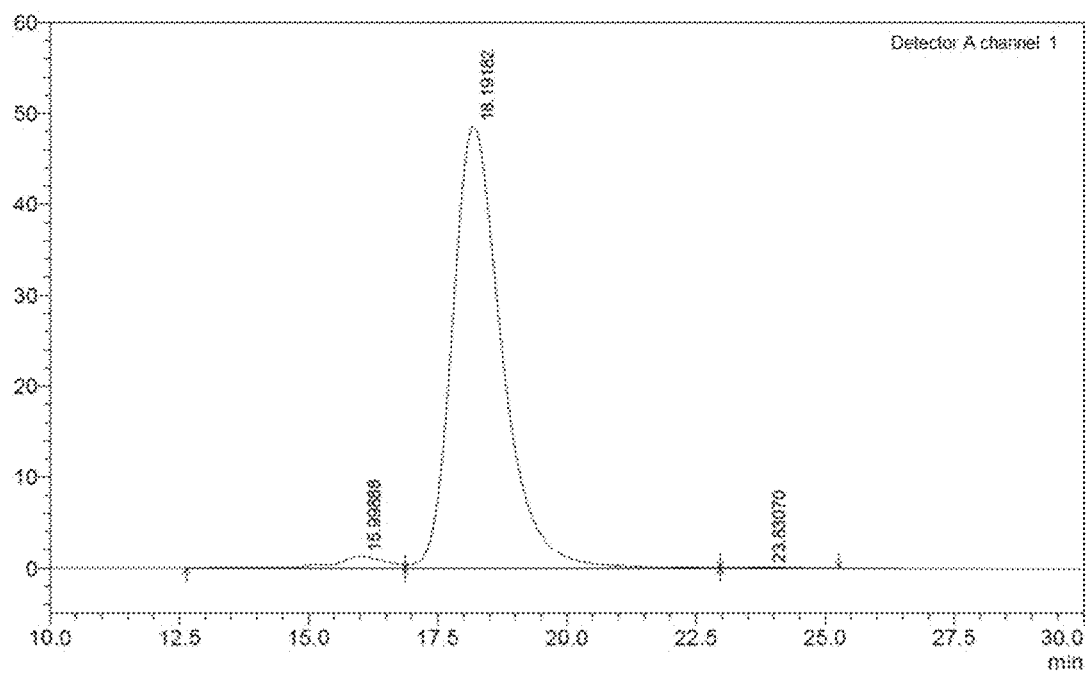
FIG. 2. SEC-HPLC chromatograph of purified FP-B protein.

Construction of an Expression Plasmid Encoding the FVIII Fusion Protein

The gene sequences encoding the FVIII signal peptide, mature protein, flexible peptide linker, rigid CTP unit, and human IgG vFc variant were artificially codon-optimized for expression in CHO cells and artificially synthesized. The synthesized full-length DNA fragment of the fusion protein had a SpeI restriction site at the 5' end and a BamHI restriction site at the 3' end. The full length DNA fragment was inserted into the corresponding restriction sites of the pUC57 transfer vector and verified by DNA sequencing.

The full-length gene fragment of the fusion protein obtained above was cloned from an intermediate vector into the corresponding restriction sites of an expression plasmid PTY1A1 to construct a high expression plasmid of the fusion protein. The PTY1A1 plasmid was derived from pcDNA3.1 by modification. The PTY1A1 plasmid contained, but was not limited to, the following important expression elements: 1) a human cytomegalovirus early promoter and an enhancer needed for exogenous high-expression in mammalian cells; 2) double screening markers with kanamycin resistance in bacteria and G418 resistance in mammalian cells; 3) a murine dihydrofolate reductase (DHFR) gene expression cassette. When the host cell type was DHFR gene deficient, methotrexate (MTX) could co-amplify the fusion gene with the DHFR gene (see U.S. Pat. No. 4,399,216). The fusion protein expression plasmid was transfected into a mammalian host cell line. The preferred host cell line was the DHFR enzyme-deficient CHO cell line in order to achieve stable and high level of expression (see U.S. Pat. No. 4,818,679). Two days after transfection, the medium was replaced with a screening medium containing 0.6 mg/mL of G418. The cells were seeded in a 96-well plate at a certain concentration (5000-10000 viable cells/well) and were cultured for 10-14 days until large discrete cell clones appeared. The transfectants resistant to the selected antibiotic were screened by the ELISA assay. The wells producing high levels of the fusion protein were subcloned by limiting dilution on the 96-well culture plate.

As shown in Table 1, the present invention constructed a series of hFVIII fusion proteins, which contained linkers of different lengths, rigid CTP units of different composition, and IgG Fc variant (vFc) elements of several different subtypes. To verify that at least one rigid CTP unit of different lengths could significantly improve the activity of the fusion protein, we constructed the fusion proteins, FP-A, FP-B, FP-C, FP-D and FP-E. The amino acids and coding nucleotides of FP-B were shown in FIG. 1. To verify the importance of the rigid CTP unit to the activity of the fusion protein, we also constructed the Fc fusion proteins FP-G and FP-H without the rigid CTP unit. The expression plasmids were constructed as above. In addition, we also constructed FP-F that had the rigid CTP unit at the C-terminus of Fc to verify the importance of the position of the rigid CTP unit. See table 1 for details. The amino acid sequences for each component were shown in the sequence listings.

TABLE 1

Compositions of various FVIII fusion proteins

| Code | Composition of FVIII fusion protein series (from N to C terminus) |
|---|---|
| FP-A | FVIII-L3-CTP1-vFcγ1 |
| FP-B | FVIII-L2-CTP2-vFcγ2-3 |
| FP-C | FVIII-L5-CTP4-vFcγ4 |
| FP-D | FVIII-L1-CTP3-CTP3-vFcγ2-2 |
| FP-E | FVIII-L4-CTP3-vFcγ2-1 |
| FP-F | FVIII-L2-vFcγ2-3-CTP2 |
| FP-G | FVIII-L1-vFcγ2-3 |
| FP-H | FVIII-L4-vFcγ2-3 |

Example 2

Transient Expression and Activity Determination of Various Fusion Proteins

Eight expression plasmids obtained in Example 1 were respectively transfected into 3×107 CHO-K1 cells using the DNAFect LT reagent (ATGCell) in a 30 mL shake flask, and the transfected cells were cultured in serum-free growth medium containing 1000 ng/mL of vitamin K1 for 5 days. The concentration of the fusion protein in the supernatant was measured and its activity was determined by the method described in Example 6 or 7. The ELISA results showed that the transient protein expression levels of the eight plasmids were similar under these conditions, but the coagulation activities of these fusion proteins showed large differences.

We defined the molar specific activity of FP-A to 100%. The fusion protein FP-G secreted in the cell culture supernatant was mostly in the form of non-active aggregates. The FP-F and FP-H plasmids expressed low-activity fusion proteins, with their activities being about 20.5% and 15.2% of that of FP-A, respectively. Similar to FP-G, most of the fusion proteins FP-F and FP-H were in the form of aggregates. Moreover, the fusion proteins FP-F, FP-G and FP-H were prone to degradation, showing poor stability. It was reported that the lipid binding region of FVIII (amino acids 2303-2332) was critical to its function, and small conformational changes in this region caused protein aggregation and led to loss of activity (Gilbert G E et al., Biochemistry, 1933,32(37): 9577-9585). Therefore, we speculated that the conformations of the lipid binding regions in the FVIII fusion proteins FP-F, FP-G and FP-H were changed due to influence of the C-terminal Fc ligands, which led to the aggregation of the proteins and significant reduction of the activities. The activities of FP-B, FP-C, FP-D and FP-E containing CTP were 113.4%, 96.0%, 87.4% and 93.7% of that of FP-A, respectively.

Based on the activity differences between FP-B, FP-F and FP-H, it could be understood that by only extending the length of the peptide linker, neither the activity of the fusion protein could be effectively improved, nor the problem of the fusion protein being prone to aggregation and degradation could be solved. The addition of the CTP unit resulted in a significant increase in the activity of the fusion protein FP-B. We speculated that the reasons were as follows. Overlong flexible peptide linkers gave FVIII higher flexibility, such that FVIII could rotate freely relative to the Fc domain. As a result, the three-dimensional structure of FVIII was located close to the Fc domain. On one hand, the addition of the rigid CTP unit between FVIII and Fc is equivalent to the addition of a rigid peptide linker, allowing the FVIII and Fc domains away from each other. More importantly, compared to the random coil of the flexible peptide linker, the rigid CTP peptide containing multiple glycosyl side chains could form a stable steric conformation, and effectively separate the different functional regions of the fusion protein. Thus, the FVIII and Fc portions were allowed to fold independently into correct three-dimensional conformations, maintaining high activities. We verified the correctness of this hypothesis by comparing the activities of FP-B and FP-F. The activity of FP-F was less than 20% of that of FP-B. In FP-F the rigid CTP unit was placed at the C-terminus of Fc, while in FP-B the rigid CTP unit was placed at the N-terminus of Fc. The above results demonstrated that the rigid CTP unit was critical to the activity of the fusion protein, and placing the rigid CTP unit at the N-terminus of Fc could effectively improve the activity of the fusion protein.

Example 3

Screening for Stably Transfected Cell Lines with High Expression of Fusion Proteins The expression plasmids of FP-A, FP-B, FP-C, FP-D and FP-E were transfected into mammalian host cell lines to express the FVIII fusion proteins. The preferred host cell was the DHFR-deficient CHO cell in order to maintain a stable high level of expression (U.S. Pat. No. 4,818,679). One preferred method of transfection was electroporation, and other methods might be used, including calcium phosphate co-deposition, liposome transfection, microinjection, etc. For the electroporation method, used was a Gene Pulser Electroporator (Bio-Rad Laboratories) set at 300 V voltage and 1050 µFd capacitance. 50 µg of PvuI linearized expression plasmid was added to 2 to $3\times10^7$ cells placed in a cuvette. After electroporation, the cells were transferred to a shake flask containing 30 mL of growth medium. Two days after transfection, the medium was replaced with a screening medium containing 0.6 mg/mL of G418. The cells were seeded in a 96-well plate at a certain concentration (5000-10000 viable cells/well) and were cultured for 10-12 days until large discrete cell clones appeared. The anti-human IgG Fc ELISA assay was used to screen the transfectants that were resistant to the selected drug. The quantitative determination of the fusion protein expression could also be performed using the anti-FVIII ELISA assay. Then wells producing high levels of fusion proteins were subcloned by limiting dilution.

It was preferred to perform co-amplification by utilizing the DHFR gene which could be inhibited by the MTX drug to achieve higher level expression of the fusion protein. In growth medium containing increasing concentrations of MTX, the transfected fusion protein gene was co-amplified with the DHFR gene. The DHFR positive subclones were subjected to limiting dilution and transfectants capable of growing in medium containing up to 6 µM MTX was screened out by progressive pressure. The secretion efficiencies thereof were determined and the cell lines with high expression of exogenous proteins were screened out. The cell lines with a secretion efficiency of more than about 1 (preferably about 3) IU per $10^6$ cells in 24 h were adapted to suspension culture using serum-free medium, and then the fusion protein was purified from the conditioned medium.

In the examples below, FP-B was taken as an example to illustrate the method for fermentation and purification of the fusion protein. The methods for fermentation and purification of FP-A, FP-C, FP-D and FP-E were the same as that of FP-B, and would not be described here again.

Example 4

Production of the Fusion Protein

The high expression cell strain obtained in Example 3 was first acclimated to serum-free medium in a petri dish and then transferred to a shake flask for suspension domestication. After the cells were adapted to these culture conditions, the cells were fed-batched in a 300 mL shake flask or cultured by replacing the medium daily to simulate a perfusion system. The CHO-derived cell strain expressing the fusion protein FP-B obtained from Example 3 was fed-batched in a 300 mL shake flask for 14 days, and the cumulative yield of the expressed recombinant fusion protein reached 200 mg/L, while the highest viable cell density could reach up to $15\times10^6$ cells/mL. 1000 mL shake flasks could be used for producing more fusion proteins. In another culture method, the above CHO-derived cell strain was cultured in a 100 mL shake flask with the medium changed daily. The expressed recombinant fusion protein reached a cumulative yield of about 20 mg/L per day. The highest viable cell density in the shake flask was up to $30\times10^6$ cells/mL. The biological activities of the recombinant fusion proteins produced by the above two methods were equivalent.

Example 5

Purification and Qualitative Analysis of the Fusion Protein

The invention mainly used a four-step chromatography procedure to purify the fusion protein FP-B, i.e., affinity chromatography, hydrophobic chromatography, anion exchange chromatography, and molecular sieve chromatography. In this example, the AKTA pure 25 M system (GE Healthcare, USA) was the instrument used for protein purification. The reagents used in this example were all purchased from Sinopharm Chemical Reagent Co., which were of analytical grade.

Step 1, affinity chromatography: Sample capture, concentration and removal of part of contaminants were performed by using the alkali-resistant Protein A Diamond resin (Bestchrom, Shanghai) or other commercially available recombinant protein A affinity chromatography resins. The other resins included, for example, MabSelect (GE Healthcare), MabSelect SuRe (GE Healthcare), Toyopearl AF-rProtein A-650F (Tosoh Bioscience), rProtein A Beads (Smart-Lifesciences, Changzhou, China), MabPurix (Sepax Technologies), and Protein A Ceramic HyperD (Pall Life Sciences). The column was equilibrated at a linear flow rate of 50-100 cm/h with 3-5 column volumes (CVs) of equilibration buffer: 20 mM His-HCl, 150 mM NaCl, 5 mM CaCl2, 0.02% Tween-80, pH 6.8-7.2. The centrifuged fermentation supernatant was loaded onto the column at no more than 50000 IU protein/mL resin at a linear flow rate of 50-100 cm/h. After loading, the column was equilibrated with 3 to 5 CVs of the equilibration buffer at a linear flow rate of 50-100 cm/h to wash off unbound materials. The column was then washed with 3-5 CVs of decontamination buffer 1: 20 mM His-HCl, 2 M NaCl, 4 M urea, 5 mM CaCl2, 0.02% Tween 80, pH 6.8-7.2, at a linear flow rate of 50-100 cm/h to remove part of contaminants. The column was equilibrated with 3-5 CVs of the equilibration buffer at a linear flow rate of 50-100 cm/h. The column was further washed with 3-5 CVs of decontamination buffer 2: 20 mM His-HCl, 5 mM EDTA, 150 mM NaCl, 30% ethylene glycol, 5 mM CaCl2, 0.02% Tween 80, pH 6.8-7.2, at a linear flow rate of 50-100 cm/h to remove part of contaminants. The column was equilibrated with 3-5 CVs of the equilibration buffer at a linear flow rate of 50-100 cm/h. The target product was then eluted and collected with the elution buffer: 20 mM His-HCl, 5 mM CaCl2, 0.02% Tween 80, 50% ethylene glycol, pH 5.0 at a linear flow rate of not higher than 50 cm/h. Tris, pH 9.0 was added into the elute to adjust the pH to neutral (7.0-8.0).

Step 2, hydrophobic chromatography: The Butyl Bestarose HP resin (Bestchrom, Shanghai) or other commercially available hydrophobic chromatography resins were used in the intermediate purification step to reduce the amount of aggregates. The other resins included Butyl Sepharose HP (GE Healthcare), Toyopearl Butyl-650 (Tosoh Bioscience), Butyl Beads 4FF (Smart-Lifesciences, Changzhou, China), Generic MC 30-HIC Butyl (Sepax Technologies), and Fractogel EMD Propyl (Merck). The elute of the first step affinity chromatography still contained a certain proportion of aggregates. The aggregates were formed due to a variety of reasons. Some of the aggregates contained proteins still in native conformation, while others contained proteins whose conformation had been changed. The aggregates in different conformational forms showed significant differences in the biological activity, leading to great interference in the activity analysis. Thus, after protein capture in the first purification step was completed, the aggregates needed to be removed next. After target protein aggregation, Non-aggregates and aggregates displayed different properties including the charge characteristics and hydrophobicity. The difference in hydrophobicity was used to separate the two. Since the last purification step was molecular sieve chromatography, the fusion protein captured in the first step affinity chromatography was further purified with Butyl HP to perform a second purification step in order to partially remove the aggregates, so that the content of aggregates was less than 10%. First, the column was equilibrated with 3-5 CVs of equilibration buffer: 20 mM His-HCl, 1.5 M NaCl, 5 mM CaCl2, 0.02% Tween 80, pH 6.8-7.2 at a linear flow rate of 50-100 cm/h. The affinity-captured sample was diluted twice with the equilibration buffer to reduce the organic solvent content, and then added to the sample was an equal volume of concentrated buffer: 20 mM His-HCl, 3 M NaCl, 5 mM CaCl2, 0.02% Tween 80, pH 6.8-7.2. The sample was then loaded onto the column at less than 20000 IU protein/mL resin. After loading, the column was washed with 3-5 CVs of the equilibration buffer at a linear flow rate of 50-100 cm/h, and washed with 3-5 CVs of wash buffer: 20 mM His-HCl, 1.5 M NaCl, 5 mM CaCl2, 0.02% Tween 80, 20% ethylene glycol, pH 6.8-7.2, to remove some of the aggregates. Finally, the target protein was eluted with the elution buffer: 20 mM His-HCl, 5 mM CaCl2, 0.02% Tween 80, 50% ethylene glycol, pH 6.8-7.2, eluting at a linear flow rate of not higher than 60 cm/h, and the eluted fractions were collected and analyzed by SEC-HPLC. The target fractions with the non-aggregates percentage greater than 90% were combined and subjected to the next step purification.

Step 3, anion exchange chromatography: The Q-HP resin (Bestchrom, Shanghai) or other commercially available anion exchange chromatography resins were used in the intermediate purification step to separate structural variants and further remove contaminants such as HCP, DNA, etc. The other resins included Q HP (GE Healthcare), Toyopearl GigaCap Q-650 (Tosoh Bioscience), DEAE Beads 6FF (Smart-Lifesciences, Changzhou, China), Generik MC-Q (Sepax Technologies), Fractogel EMD TMAE (Merck), and Q Ceramic HyperD F (Pall Life Sciences). First, the column was washed with 3-5 CVs of equilibration buffer: 20 mM His-HCl, 200 mM NaCl, 5 mM CaCl2, 0.02% Tween 80, pH 6.8-7.2 at a linear flow rate of 50-100 cm/h. The target protein isolated by the second step hydrophobic chromatography was diluted twice for reducing the organic solvent content, and was loaded onto the column at less than 5000-10000 IU protein/mL resin. After loading, the column was washed with 3-5 CVs of the equilibration buffer at a linear flow rate of 50-100 cm/h, followed by elution with a linear gradient of salt concentration using the elution buffer: 20 mM His-HCl, 1 M NaCl, 5 mM CaCl2, 0.02% Tween 80, pH 6.8-7.2. The elution condition was a gradient from 0 to 100% elution buffer over 2 h at a linear flow rate of no higher than 50 cm/h. The eluted fractions were collected and analyzed for protein content, SEC-HPLC, activity and HCP content. After the protein concentration and activity were determined, the specific activity of the protein was calculated as about 10000 IU/mg.

Step 4, molecular sieve chromatography: The Chromdex 200 prep grade resin (Bestchrom) or other commercially available molecular sieve resins (e.g., Superdex 200 from GE Healthcare) were used for separation, with the goal to reduce the aggregates content to <5% and further reduce the key contaminant content. The column was washed with 2 CVs of equilibration buffer: 20 mM His-HCl, 200 mM NaCl, 5 mM CaCl2, 0.02% Tween 80, pH 6.8-7.2 at a linear flow rate of 20-40 cm/h. The sample volume loaded was no more than 3% of the column volume. The protein sample was eluted at a linear flow rate of 20 cm/h, and the eluted fractions were collected and subjected to SEC-HPLC analysis followed by combining.

Figure 3:
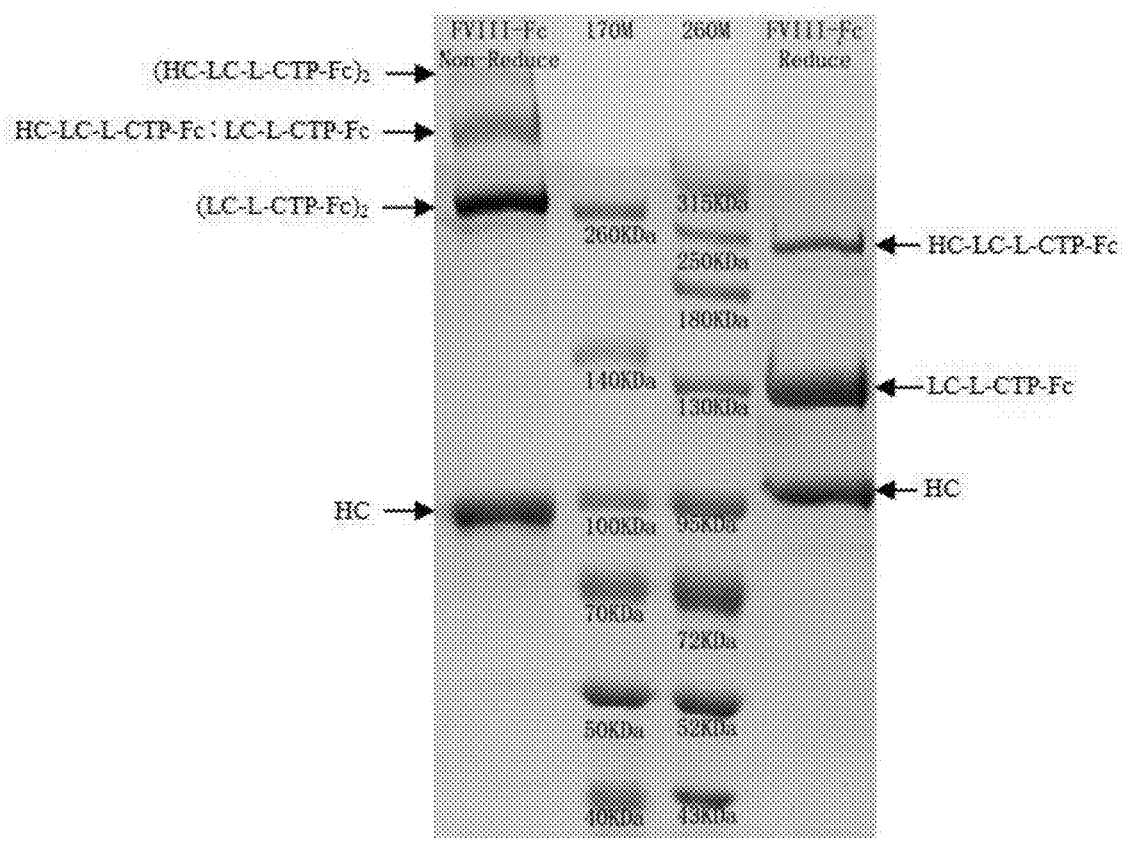
FIG. 3. SDS-PAGE analysis of purified FP-B protein.

The SEC-HPLC purity analyses and SDS-PAGE electrophoresis of the purified FP-B were shown in FIGS. 2 and 3, respectively. The SEC-HPLC results showed that the purity of the main peak of the purified fusion protein FP-B was above 97%. The band patterns of the SDS-PAGE electrophoresis appeared as expected. The non-reducing electrophoresis lane contained a band for the unprocessed fusion protein FP-B (390 kDa), a band for HC-LC-L-CTP-Fc:LC-L-CTP-Fc (300 kDa), of which one heavy chain fragment of FVIII was lost during electrophoresis, a band for the dimer (LC-L-CTP-Fc)2 (210 kDa), of which the two heavy chain fragments were lost during electrophoresis, and a band for the heavy chain fragment HC (90 kDa). The reducing electrophoresis lane contained a band for HC-LC-L-CTP-Fc (190 kDa), a band for LC-L-CTP-Fc (105 kDa), and a band for the single chain HC (90 kDa).

Example 6

Indirect Determination of In Vitro Activity of the Fusion Protein by the Chromogenic Substrate Assay The activity of the FVIII fusion protein could be determined by the chromogenic substrate assay. In this example the Chromogenix Coatest SP FVIII kit (Chromogenix, Ref. K824086) was used and the assay principle was as follows. When activated by thrombin, FVIIIa bound to FIXa in the presence of phospholipid and calcium ions to form an enzyme complex, which in turn activated factor X into its active form, Xa. The activated factor Xa then decomposed its specific chromogenic substrate (Chromogenix S-2765), releasing the chromophore pNA. The amount of pNA produced was measured at 405 nm, and thus the activity level of FXa which was directly proportional to the amount of pNA was obtained. As the amount of factor IXa and factor X in the assay system was excessive and constant, the activity of FXa was only directly related to the amount of FVIIIa. The specific activities of the FVIII fusion proteins were about 6000-10000 IU/mg as determined by this assay.

Example 7

Direct Determination of the Biological Activity of the Fusion Protein by the Clotting Assay The clotting assay for determining the biological activity of FVIII was based on the property of FVIII to correct the prolonged clotting time of FVIII-deficient plasma. Using the Coagulation Factor VIII Deficient Plasma kit (Cat. No. OTXW17) of the German company Siemens, the method for determining the FVIII activity was as follows. First, the FVIII standard with a known potency from National Institutes for Food and Drug Control (China) was diluted to 10 IU/mL with 5% FVIII-deficient plasma, which was then further diluted 10 times, 20 times, 40 times, and 80 times, respectively. The activated partial thromboplastin time (APTT) was determined by an automatic hemagglutination analyzer (CA500, Sysmex). A standard curve was established with the FVIII standard by plotting a linear regression of the logarithm of the potencies (IU/mL) of the FVIII standard solutions vs. the logarithm of their corresponding clotting times (s). Then the test sample was properly diluted and mixed with the FVIII-deficient substrate plasma to perform the APTT assay. The potency of the test FVIII sample (IU/mL) could be calculated by substituting the clotting time into the standard curve equation. Thus the specific activity of the test FVIII sample could be calculated in the unit of IU/mg. The specific activities of the FVIII fusion proteins were about 6000-10000 IU/mg as determined by this assay.

Example 8

Hemostatic Effect of Fusion Proteins on Acute Hemorrhage in Hemophilia A Mice

We evaluated the hemostatic activity of the fusion protein FP-B prepared in Example 5 in a VIII factor gene-knockout homozygous HemA mouse tail clip bleeding model. Male HemA mice (8-12 weeks old, Shanghai Model Organisms Center, Inc.) were adaptively fed for one week, and then randomly divided into 6 groups. In addition, one group of HemA mice was set up as negative control, and another group of normal C57 mice was set up as positive control. To the 8 groups, different active doses of the fusion protein FP-B or the control drug Xyntha (Pfizer) were given by a single tail vein injection. Table 2 showed experimental design and animal grouping.

TABLE 2

Animal grouping regarding the hemostatic effect of fusion proteins in HemA mice

| Group number | Group | Mouse type | Quantity (each) | Dosage |
|---|---|---|---|---|
| 1 | HA control group | HemA mice | 6 | Physiological saline |
| 2 | C57 control group | C57 mice | 8 | Physiological saline |
| 3 | FP-B-270 | HemA mice | 9 | FP-B, 270 IU/kg |
| 4 | Xyntha-270 | HemA mice | 11 | Xyntha, 270 IU/kg |
| 5 | FP-B-90 | HemA mice | 9 | FP-B, 90 IU/kg |
| 6 | Xyntha-90 | HemA mice | 9 | Xyntha, 90 IU/kg |
| 7 | FP-B-30 | HemA mice | 11 | FP-B, 30 IU/kg |
| 8 | Xyntha-30 | HemA mice | 10 | Xyntha, 30 IU/kg |

Before administration, each of the mice were anesthetized by injecting intraperitoneally with 1.0% pentobarbital sodium (Sigma) at a dose of 0.1 mL/10 g, and then placed on a 37° C. heating pad to maintain body temperature. The tail of the mouse was immersed in warm water at 37° C. for 10 min to expand the tail vein, and then the corresponding dose in Table 2 was administered. 10 min after administration, the tail was cut off at 1.5 cm from the tail tip, and the tail was rapidly immersed in about 13 mL of preheated saline contained in a centrifuge tube. Started timing. If bleeding stops within 30 min, recorded the bleeding time and volume. If the bleeding time was more than 30 min, recorded it as 30 min. Bleeding volume (mL)=(weight of centrifuge tube after blood collection (g)−weight of centrifuge tube before blood collection (g))/1.05. After 30 min, removed the tail from the tube containing saline. Within 24 h, observed and recorded recurrent bleeding every 10 min and recorded the number of surviving mice. All data were expressed as mean±standard error ($\bar{x}$±SEM). The t-test was used to compare the experimental groups. The analysis software was GraphPad Prism 5.0. $P<0.05$ was considered statistically significant.

Figure 4:
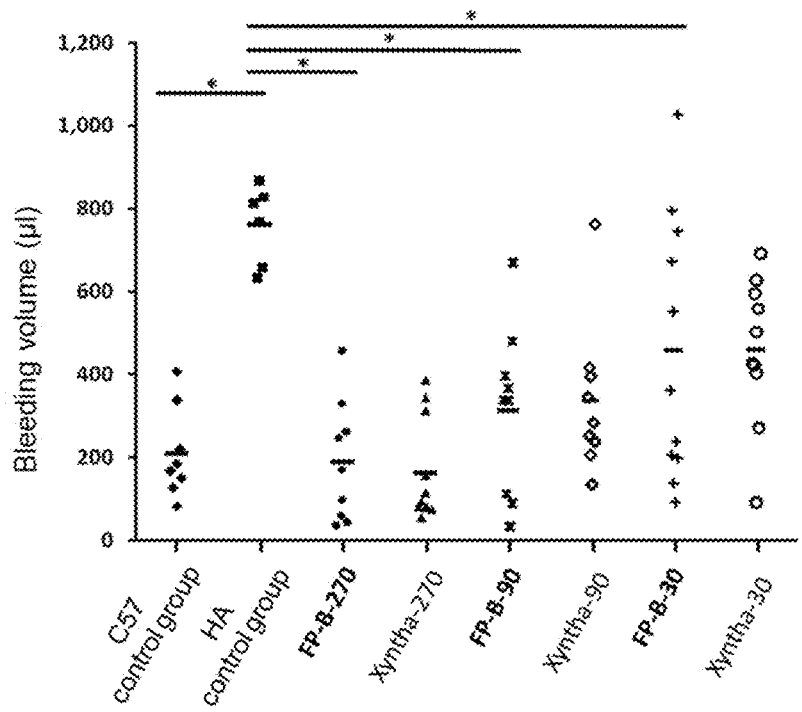
FIG. 4. Bleeding volume (µl) for each mouse after tail transection. Note: *p<0.05, **p<0.01.
Figure 5:
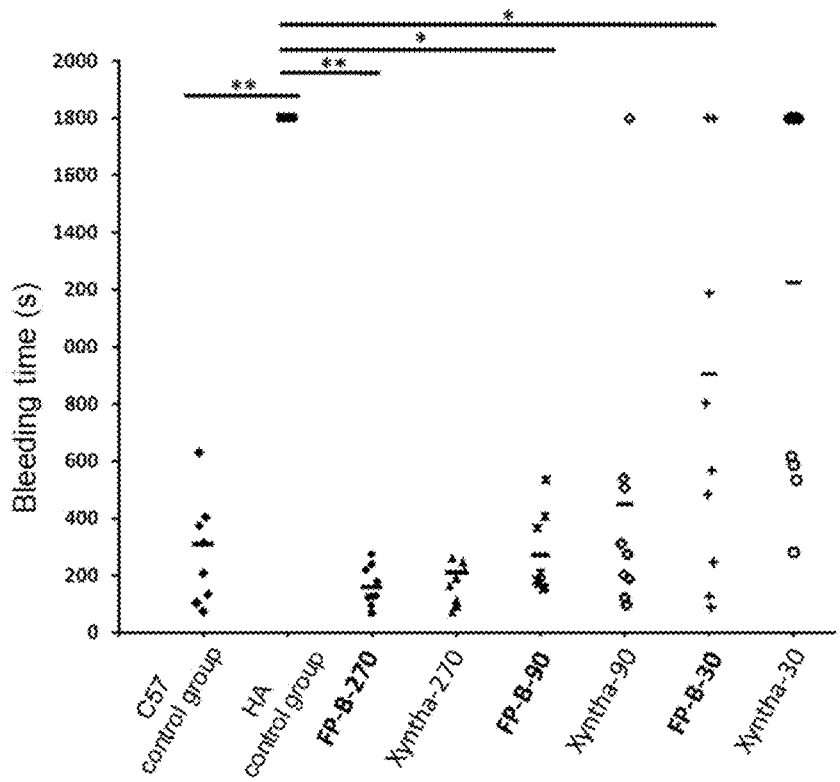
FIG. 5. Bleeding time (s) for each mouse after tail transection. Note: *p<0.05, **p<0.01.

FIGS. 4 and 5 showed statistical analyses of bleeding time and volume for each group of the animals. 10 min after giving the HemA mice 270 IU/kg of FP-B, the bleeding time and volume of the FP-B-270 group were close to those of the C57 control group. The procoagulant effect of FP-B was evident, indicating that FP-B could be used as an effective coagulation agent for acute hemorrhage in patients with coagulation factor deficiencies such as hemophilia. When the mice were given 90 IU/kg of FP-B, the bleeding time and volume of the FP-B-90 group were also close to those of the C57 control group. There was no significant difference in bleeding volume between the HemA mice given the same amount of active dose of FP-B and Xyntha, but the bleeding time of the FP-B group at each dose was slightly less than that of the Xyntha group, indicating that FP-B may have a certain efficacy advantage compared to Xyntha. Compared with the 30 IU/kg FP-B group, the 90 IU/kg FP-B group showed a significantly shorter bleeding time ($p<0.05$), and the 270 IU/kg FP-B group showed a significantly shorter bleeding time ($p<0.05$) and also a significantly reduced bleeding volume ($p<0.05$). This indicated that the fusion protein FP-B had a dose-effect relationship on the hemostasis of acute hemorrhage in HemA mice (see Table 3 for details).

According to the postoperative recovery, when given the same amount of active dose of FP-B and Xyntha, the FP-B group at each dose had a higher mouse survival rate than the Xyntha group at a same active dose, indicating that the fusion protein FP-B had a more lasting effect than Xyntha (see Table 3).

TABLE 3

Bleeding time, volume, recurrent bleeding and survival rate statistics for each group of HemA mice after tail transection

| Group | FP-B | | | Xyntha | | | C57 control group | HA control group |
|---|---|---|---|---|---|---|---|---|
| | 270 IU/kg | 90 IU/kg | 30 IU/kg | 270 IU/kg | 90 IU/kg | 30 IU/kg | | |
| Bleeding volume (μL) | 189.2 ± 48.9 | 313.4 ± 68.2 | 456.5 ± 95.3 | 161.7 ± 37.2 | 336.4 ± 61.1 | 459.4 ± 56.7 | 209.3 ± 38.8 | 760.5 ± 38.9 |
| Bleeding time (s) | 160 ± 23.4 | 269 ± 46.2 | 904 ± 218.3 | 210 ± 23.3 | 448 ± 176.7 | 1224 ± 213.4 | 310 ± 66.7 | 1800b ± 0.0 |
| 24-48 h survival rate | 100% | 100% | 64%a | 91% | 78% | 50%a | 100% | 17% |

Note:
aBecause there were mice dying within 24-48 h, so the 48 h survival rate was presented.
bIf the bleeding time was more than 30 min, recorded it as 1800 s.

All documents mentioned in the present invention are hereby incorporated by reference to the same extent as if each of the documents is individually recited for reference. It is to be understood that various changes and modifications may be made by those skilled in the art upon reading the above teachings of the present invention, which also fall within the scope of the claims appended hereto.

The invention claimed is:

1. A fusion protein, wherein the fusion protein has the amino acid sequence of SEQ ID NO: 16.

2. A pharmaceutical composition comprising a pharmaceutically acceptable carrier, excipient and/or diluent, and an effective amount of a fusion protein of claim 1.

3. A method for preparing a fusion protein, including steps comprising:
   (a) introducing a DNA molecule encoding a fusion protein of claim 1 into a CHO cell to produce a CHO-derived cell line;
   (b) screening the cell strains of step (a) to obtain a high-yield cell strain expressing more than 1 IU/$10^6$ (million) cells per 24 h in its growth medium;
   (c) culturing the cell strain obtained in step (b) to express the fusion protein; and
   (d) harvesting the fermentation broth of step (c) and isolating and purifying the fusion protein.

4. A method for treating hemorrhagic diseases in patients with congenital or acquired FVIII deficiency or for treating spontaneous or surgical bleeding in patients with hemophilia A, comprising administrating an effective amount of a fusion protein of claim 1 to the patient.

* * * * *